(12) United States Patent
Shanklin et al.

(10) Patent No.: US 12,415,840 B2
(45) Date of Patent: Sep. 16, 2025

(54) MODIFIED FORM OF OLEOSIN THAT WHEN EXPRESSED IN PLANTS LEADS TO INCREASED TRIACYLGLYCEROL (OIL) ACCUMULATION

(71) Applicant: Brookhaven Science Associates, LLC, Upton, NY (US)

(72) Inventors: John Shanklin, Shoreham, NY (US); Sanket P. Anaokar, Carle Place, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 718 days.

(21) Appl. No.: 17/180,195

(22) Filed: Feb. 19, 2021

(65) Prior Publication Data
US 2021/0261632 A1  Aug. 26, 2021

Related U.S. Application Data

(60) Provisional application No. 62/979,576, filed on Feb. 21, 2020.

(51) Int. Cl.
C07K 14/415 (2006.01)
C12N 15/82 (2006.01)

(52) U.S. Cl.
CPC ........ C07K 14/415 (2013.01); C12N 15/8247 (2013.01)

(58) Field of Classification Search
None
See application file for complete search history.

(56) References Cited

U.S. PATENT DOCUMENTS

| | | | |
|---|---|---|---|
| 8,987,551 B2 | 3/2015 | Roberts et al. | |
| 2009/0133160 A1 | 5/2009 | Scott et al. | |
| 2011/0191905 A1 | 8/2011 | Bryan et al. | |
| 2012/0278951 A1* | 11/2012 | Roberts ............ | C12N 15/8261 536/23.6 |
| 2014/0031573 A1 | 1/2014 | Shanklin et al. | |
| 2015/0252378 A1 | 9/2015 | Roberts et al. | |
| 2015/0275223 A1 | 10/2015 | Roberts et al. | |
| 2015/0284726 A1 | 10/2015 | Van Heeke et al. | |

FOREIGN PATENT DOCUMENTS

WO  2008/130248 A1  10/2008

OTHER PUBLICATIONS

Winichayakul et al, In Vivo Packaging of Triacylglycerols Enhances *Arabidopsis* Leaf Biomass and Energy Density, 2013, Plant Physiology 162: 626-639 (Year: 2013).*
Uniprot A0A1S3YRU9 2017 https://www.uniprot.org/uniprotkb/A0A1S3YRU9/entry (Year: 2017).*
Uniprot G8H6H8 2012 https://www.uniprot.org/uniprotkb/G8H6H8/entry (Year: 2012).*
Uniprot Q42431 2023 https://www.uniprot.org/uniprotkb/Q42431/entry (Year: 2023).*
Huang et al, 2015, Plant Physiology 169: 453-70 (Year: 2015).*
Board et al, 2022, Biophysical Reviews 14:257-266 (Year: 2022).*
Winichayakul et al 2013 Plant Physiology 162: 626-639 (Year: 2013).*
Andrianov et al., 2010 Plant Biotechnol J 8: 277-287.
Bouvier-Nave et al., 2000 Eur J Biochem 267: 85-96.
Durrett et al., 2008 Plant J 54: 593-607.
Fortman et al., 2008 Trends Biotechnol 26: 375- 381.
Hill et al., 2006 Proc Natl Acad Sci USA 103: 11206-11210.
James et al., 2010 Proc Natl Acad Sci USA 107: 17833-17838.
Mu et al., 2008 Plant Physiol 148: 1042-1054.
Petrie et al., 2012 PLoS One 7: e35214.
Santos-Mendoza et al., 2008 Plant J 54: 608-620.
Sanjaya et al., 2011 Plant Biotech J 9: 874-883.
Siloto et al., 2006 Plant Cell 18: 1961-1974.
Shimada et al., 2008 Plant J. 55(5):798-809.
Shockey et al., 2006 Plant Cell. 18, 2294-2313.
Slack et al., 1980 Biochem J. 190(3):551-561.
Slocombe et al., 2009 Plant Biotechnol J 7: 694-703.
Somerville, 2007 Biofuels. Curr Biol 17: R115-R119.
Troncoso-Ponce et al., 2013 Plant Sci 205-206: 13-19.
Tzen et al., 1992 J Biol Chem 267: 15626-15634.
Winichayakul S et al., 2013 Plant Physiol 162:626-639.
Yang and Ohlrogge, 2009 Plant Physio 1 150: 1981-1989.

* cited by examiner

*Primary Examiner* — Brent T Page
*Assistant Examiner* — Aleksandar Radosavljevic
(74) *Attorney, Agent, or Firm* — Dorene Price

(57) ABSTRACT

The invention provides mutant or variant oleosin polypeptides having one or more amino acid substitutions, particularly one or more arginine substitution for lysine, and having one or more amino acid deletions. The mutant oleosin polypeptides provide for higher triacylglycerol compared to wild type oleosin, including when the mutant oleosin is expressed in plants. Also provided are polynucleotides encoding the mutant oleosin(s), constructs and host cells comprising the polynucleotides, methods for producing oil bodies comprising the mutant oleosin(s) and for producing oil in host cells and plants. The invention also relates to plants, particularly transgenic or recombinantly engineered plants, expressing one or more of the mutant oleosin polypeptides, as well as seeds and oil bodies derived from the plants.

29 Claims, 8 Drawing Sheets

Specification includes a Sequence Listing.

FIGURE 3

```
                         3          12          23 27
                         △          △           △  R
OLE1(native)     MAEHYGQQQQTRAPHLQLQPRAQRVVKAATAVTAGGSLLVLSGLTLAGTVIALTIATPLL 60
OLE_KR           MAEHYGQQQQTRAPHLQLQPRAQRVVRAATAVTAGGSLLVLSGLTLAGTVIALTIATPLL
Cys_OLE1         MACHYGQQQQTCAPHLQLQPRACRVVKAATAVTAGGSLLVLSGLTLAGTVIALTIATPLL
Cys_OLE1_KR      MACHYGQQQQTCAPHLQLQPRACRVVRAATAVTAGGSLLVLSGLTLAGTVIALTIATPLL
OLE1_Cys_DEL     MA-HYGQQQQT-APHLQLQPRA-RVVKAATAVTAGGSLLVLSGLTLAGTVIALTIATPLL
OLE1_Cys_DEL_KR  MA-HYGQQQQT-APHLQLQPRA-RVVRAATAVTAGGSLLVLSGLTLAGTVIALTIATPLL
Ole1_5mod        MAEHYGQQQQT-APHLQLQPRAQRVVRAATAVTAGGSLLVLSGLTLAGTVIALTIATPLL
Ole1_3mod        MAEHYGQQQQT-APHLQLQPRAQRVVRAATAVTAGGSLLVLSGLTLAGTVIALTIATPLL
OleNative3       MAEHYGQQQQT-APHLQLQPRA-RVVRAATAVTAGGSLLVLSGLTLAGTVIALTIATPLL
OleNative12      MA-HYGQQQQTRAPHLQLQPRA-RVVRAATAVTAGGSLLVLSGLTLAGTVIALTIATPLL
OleNative23      MA-HYGQQQQT-APHLQLQPRAQRVVRAATAVTAGGSLLVLSGLTLAGTVIALTIATPLL
OleNative112     MA-HYGQQQQT-APHLQLQPRA-RVVRAATAVTAGGSLLVLSGLTLAGTVIALTIATPLL
OleNative123     MA-HYGQQQQT-APHLQLQPRA-RVVRAATAVTAGGSLLVLSGLTLAGTVIALTIATPLL
OleNative136     MA-HYGQQQQT-APHLQLQPRA-RVVRAATAVTAGGSLLVLSGLTLAGTVIALTIATPLL
OleK27           MA-HYGQQQQT-APHLQLQPRA-RVVKAATAVTAGGSLLVLSGLTLAGTVIALTIATPLL
OleK105          MA-HYGQQQQT-APHLQLQPRA-RVVRAATAVTAGGSLLVLSGLTLAGTVIALTIATPLL
OleK117          MA-HYGQQQQT-APHLQLQPRA-RVVRAATAVTAGGSLLVLSGLTLAGTVIALTIATPLL
OleK119          MA-HYGQQQQT-APHLQLQPRA-RVVRAATAVTAGGSLLVLSGLTLAGTVIALTIATPLL
OleK128          MA-HYGQQQQT-APHLQLQPRA-RVVRAATAVTAGGSLLVLSGLTLAGTVIALTIATPLL 105   112   117 119
                                                           R     △     R   R
OLE1(native)     VIFSPVLVPAVITIFLLGAGFLASGGFGVAALSVLSWIYRYLTGKHPPGADQLESAKTKL 120
OLE_KR           VIFSPVLVPAVITIFLLGAGFLASGGFGVAALSVLSWIYRYLTGRHPPGADQLESARTRL
Cys_OLE1         VIFSPVLVPAVITIFLLGAGFLASGGFGVAALSVLSWIYRYLTGKHPPGADCLESAKTKL
Cys_OLE1_KR      VIFSPVLVPAVITIFLLGAGFLASGGFGVAALSVLSWIYRYLTGRHPPGADCLESARTRL
OLE1_Cys_DEL     VIFSPVLVPAVITIFLLGAGFLASGGFGVAALSVLSWIYRYLTGKHPPGAD-LESAKTRL
OLE1_Cys_DEL_KR  VIFSPVLVPAVITIFLLGAGFLASGGFGVAALSVLSWIYRYLTGRHPPGAD-LESARTRL
Ole1_5mod        VIFSPVLVPAVITIFLLGAGFLASGGFGVAALSVLSWIYRYLTGRHPPGADQLESARTKL
Ole1_3mod        VIFSPVLVPAVITIFLLGAGFLASGGFGVAALSVLSWIYRYLTGKHPPGADQLESAKTKL
OleNative3       VIFSPVLVPAVITIFLLGAGFLASGGFGVAALSVLSWIYRYLTGRHPPGAD-LESARTRL
OleNative12      VIFSPVLVPAVITIFLLGAGFLASGGFGVAALSVLSWIYRYLTGRHPPGAD-LESARTRL
OleNative23      VIFSPVLVPAVITIFLLGAGFLASGGFGVAALSVLSWIYRYLTGRHPPGAD-LESARTRL
OleNative112     VIFSPVLVPAVITIFLLGAGFLASGGFGVAALSVLSWIYRYLTGRHPPGADQLESARTRL
OleNative123     VIFSPVLVPAVITIFLLGAGFLASGGFGVAALSVLSWIYRYLTGRHPPGAD-LESARTRL
OleNative136     VIFSPVLVPAVITIFLLGAGFLASGGFGVAALSVLSWIYRYLTGRHPPGAD-LESARTRL
OleK27           VIFSPVLVPAVITIFLLGAGFLASGGFGVAALSVLSWIYRYLTGRHPPGAD-LESARTRL
OleK105          VIFSPVLVPAVITIFLLGAGFLASGGFGVAALSVLSWIYRYLTGKHPPGAD-LESARTRL
OleK117          VIFSPVLVPAVITIFLLGAGFLASGGFGVAALSVLSWIYRYLTGRHPPGAD-LESAKTRL
OleK119          VIFSPVLVPAVITIFLLGAGFLASGGFGVAALSVLSWIYRYLTGRHPPGAD-LESARTKL
OleK128          VIFSPVLVPAVITIFLLGAGFLASGGFGVAALSVLSWIYRYLTGRHPPGAD-LESARTRL 123 128    136
                 R
                 △   R      △
OLE1(native)     ASKAREMKDRAEQFSQQPVAGSQTS     145
OLE_KR           ASRAREMRDRAEQFSQQPVAGSQTS
Cys_OLE1         ASCAREMKDRAEQFSCQPVAGSQTS
Cys_OLE1_KR      ASCAREMRDRAEQFSCQPVAGSQTS
OLE1_Cys_DEL     AS-AREMKDRAEQFS-QPVAGSQTS
OLE1_Cys_DEL_KR  AS-AREMRDRAEQFS-QPVAGSQTS
Ole1_5mod        AS-AREMKDRAEQFSQQPVAGSQTS
Ole1_3mod        AS-AREMKDRAEQFSQQPVAGSQTS
OleNative3       AS-AREMRDRAEQFS-QPVAGSQTS
OleNative12      AS-AREMRDRAEQFS-QPVAGSQTS
OleNative23      AS-AREMRDRAEQFS-QPVAGSQTS
OleNative112     AS-AREMRDRAEQFS-QPVAGSQTS
OleNative123     ASKAREMRDRAEQFS-QPVAGSQTS
OleNative136     AS-AREMRDRAEQFSQQPVAGSQTS
OleK27           AS-AREMRDRAEQFS-QPVAGSQTS
OleK105          AS-AREMRDRAEQFS-QPVAGSQTS
OleK117          AS-AREMRDRAEQFS-QPVAGSQTS
OleK119          AS-AREMRDRAEQFS-QPVAGSQTS
OleK128          AS-AREMKDRAEQFS-QPVAGSQTS
```

FIGURE 4

```
                        *           Δ      R
             Δ        Δ
Ole1 BNL     MAEHYGQQQQTRAPHLQ-LQPRAQRVVKAATATAVTAGGSLLIVLSGLTLAGTVIALTIATPLL    60
Ole Sesamum  MAEHYGQQQQTRAPHPQ-LQPRAQRVVKAATATAVTAGGSLLIVLSGLTLAGTVIALTIATPLL
Ole Citrus   MAEHYQPHEQTQ---LQSRQPRSHQVVKAATATAVTAGGSLLIVLSGLTMAGTVIALTIATPLL
Ole Nicotiana MADYGQQHTQHQQLNSVQQPRSHQMVKAATATAVTAGGSLLIVLSGLTLAGTVIALTVATPLL
Ole Punica   MAEHQA------HGQ-HQPRSHQVVKAATATAVTAGGSLLIVLSGLTLAGTVIALTIATPLL

*          *  *
                                                    R       Δ  R  R
Ole1 BNL     VIFSPVLVPAVITIFLLGAGFLASGGFGVAALSVLSWIYRYLTGKHPPGADQLESAKTKL   120
Ole Sesamum  VIFSPVLVPAVITIFLLGAGFLASGGFGVAALSVLSWIYRYLTGKHPPGADQLESAKTKL
Ole Citrus   VICSPVLVPAVITVSLLIMGFLASGGFGVAAISVLSWIYRYVTGHPPGADQLEQARMKL
Ole Nicotiana VIFSPVIVPAVITIFMLVSGFLASGGFGVAAISVLSWIYRYVTGKRPPGADQLEHARHRL
Ole Punica   VIFSPVLVPAVITVALLTMGFLASGGFGVAALTVLSWIYRYVTGKHPPGADQIDHARMKL

*
             R
             Δ        Δ
Ole1 BNL     ASKAREMKDRAEQFSQQPVAGSQTS                                      145
Ole Sesamum  ASKAREMKDRAEQFSQQPVAGSQTS
Ole Citrus   ASKAREMRDRAEQFGQQSTGSQPGS
Ole Nicotiana ATKAGEMKDRAQEFGQQHVTGTQQG
Ole Punica   ASKAREMKDRAEQFGQQHLTTGQQQTS
```

FIGURE 6
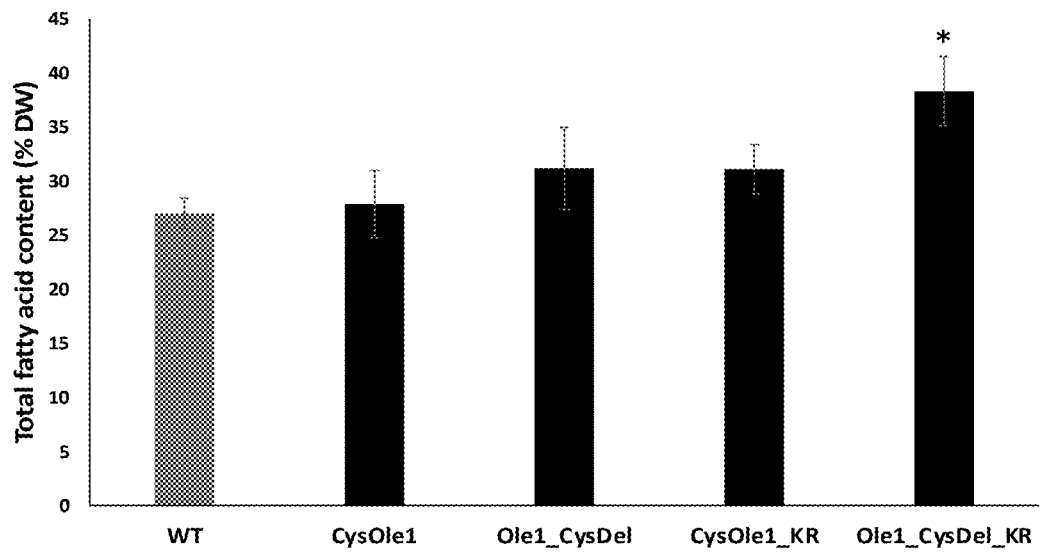
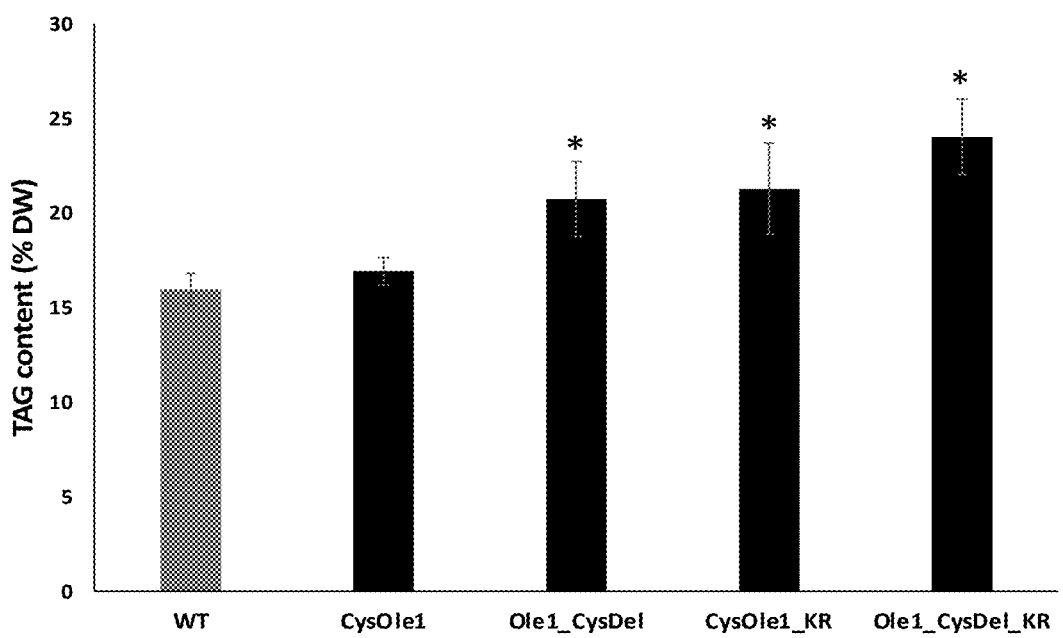

FIGURE 7
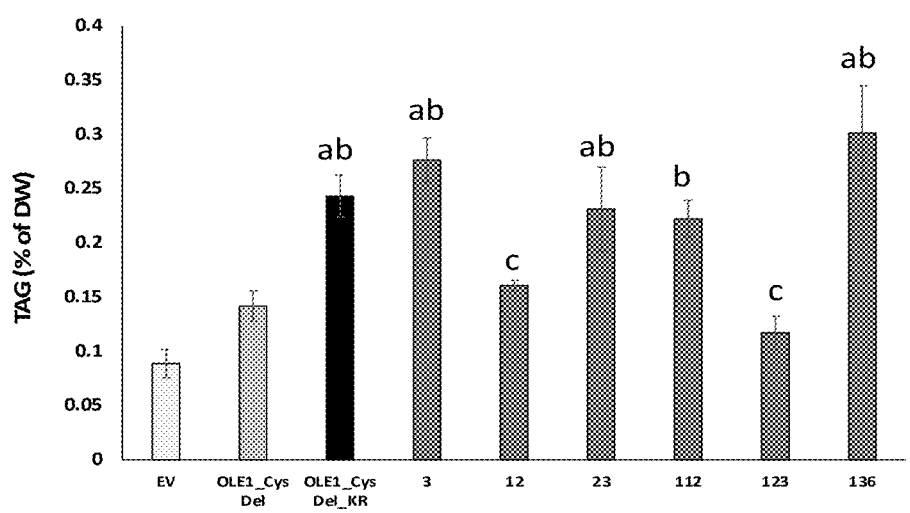
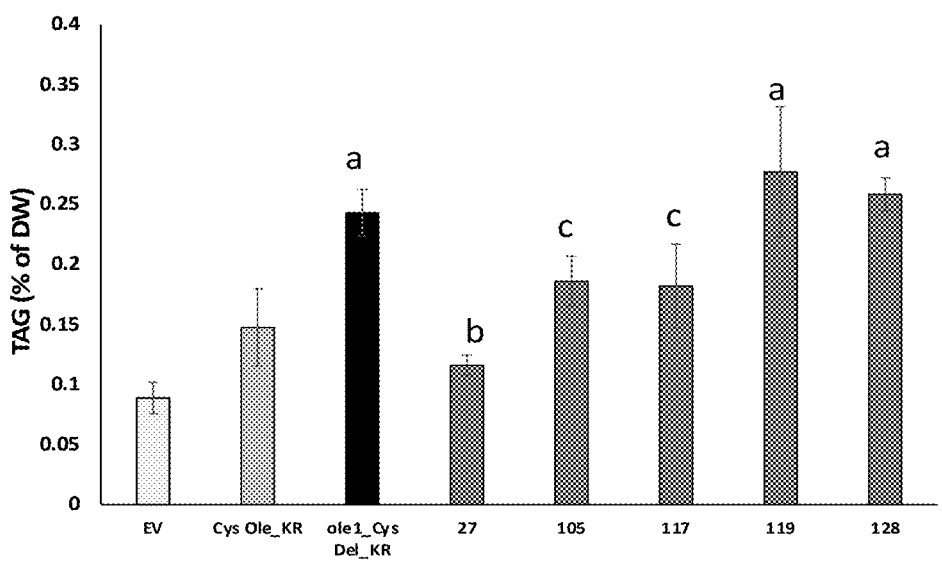

FIGURE 8
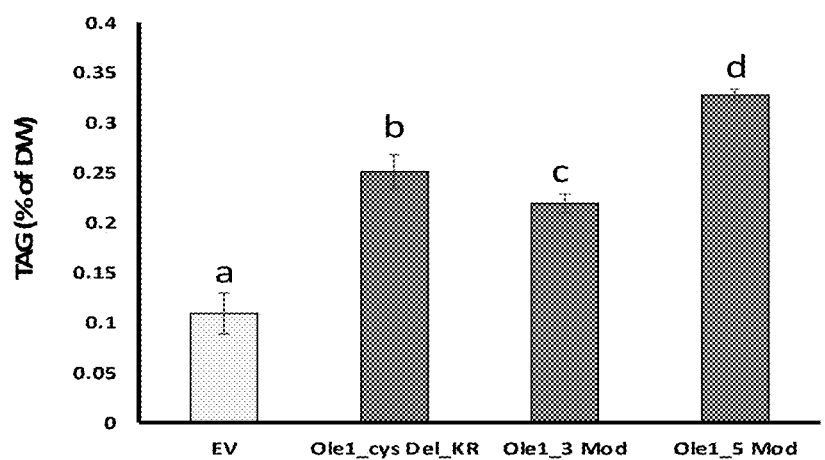
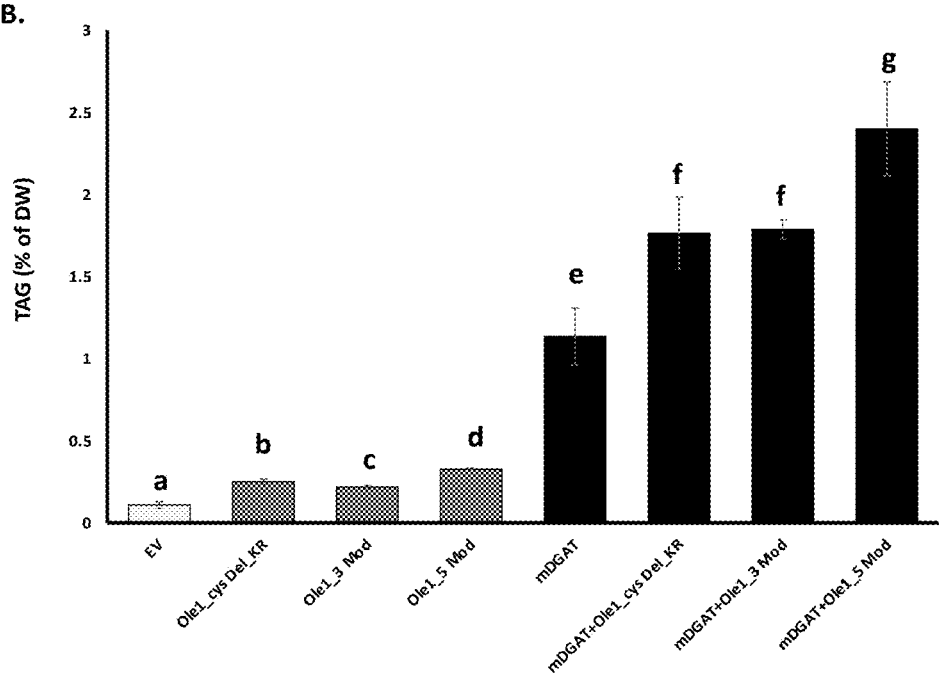

MODIFIED FORM OF OLEOSIN THAT WHEN EXPRESSED IN PLANTS LEADS TO INCREASED TRIACYLGLYCEROL (OIL) ACCUMULATION

CROSS REFERENCE TO RELATED APPLICATIONS

The present application claims priority from U.S. provisional application Ser. No. 62/979,576 filed Feb. 21, 2020, the disclosure of which is incorporated herein by reference in its entirety.

GOVERNMENT SUPPORT

This invention was made with Government support under contract number DE-SC0012704, awarded by the U.S. Department of Energy. The Government has certain rights in the invention.

FIELD OF THE INVENTION

The present invention relates generally to mutant or variant oleosin polypeptides having one or more amino acid substitutions, particularly one or more arginine substitution for lysine, and having one or more amino acid deletions. The mutant oleosin polypeptides provide for higher triacylglycerol compared to wild type oleosin, including when the mutant oleosin is expressed in plants. The invention also relates to plants, particularly transgenic or genetically engineered plants, expressing one or more of the mutant oleosin polypeptides, as well as seeds and oil bodies derived from the plants.

BACKGROUND OF THE INVENTION

In nature, flowering plants efficiently store energy in their seeds through the accumulation of oil, particularly triacylglycerol (TAG), and store it in discreet oil bodies by embedding a phospholipid protein monolayer around the oil body. These seed crops have been used in a variety of agricultural applications as feed and also as a feedstock source for biofuels. Lipids have approximately double the energy content on a per weight basis of either proteins or carbohydrates, therefore many efforts have been focused on raising the oil content of various species, notably and particularly plants.

Although liquid biofuels offer considerable promise, the reality of utilizing biological material is tempered by competing uses and the quantities available. Triacylglycerol (TAG) is a neutral lipid with twice the energy density of cellulose and can be used to generate biodiesel, a high-energy-density desirable biofuel with a simple and efficient manufacturing process (Hill et al., 2006 Proc Natl Acad Sci USA 103:11206-11210; Granda et al., 2007 Environ Prog 26:233-250; Somerville, 2007 Biofuels. Curr Biol 17: R115-R119; Fortman et al., 2008 Trends Biotechnol 26:375-381; Ohlrogge et al., 2009 Science 324:1019-1020; Chapman et al., 2013 Plant Sci 207:128-134; Troncoso-Ponce et al., 2013 Plant Sci 205-206:13-19). Consequently, engineering plants to accumulate TAG in vegetative tissues and elevating the TAG content of oleaginous yeast and bacteria is the focus of multiple research groups.

A variety of strategies to engineer TAG accumulation in vegetative tissues and microorganisms have been explored including the stimulation of fatty acid biosynthesis and TAG production by overexpressing seed development transcription factors LEAFY COT-YLEDONI (LEC1), LEC2, and WRINKLED1 (WRi1) in plants (Mu et al., 2008 Plant Physiol 148:1042-1054; Santos-Mendoza et al., 2008 Plant J 54:608-620; Andrianov et al., 2010 Plant Biotechnol J 8:277-287; Sanjaya et al., 2011 Plant Biotech J 9:874-883). In other efforts, the enzyme responsible for the last and only committed step in TAG biosynthesis, diacylglycerol O-acyltransferase (DGAT) has been overexpressed in plants and also in yeast (Bouvier-Nave et al., 2000 Eur J Biochem 267:85-96; Durrett et al., 2008 Plant J 54:593-607; Andrianov et al., 2010 Plant Biot ec hn ol J 8:277-287; Beopoulos et al., 2011 Appl Microbiol Biotechnol 90:1193-1206). Further approaches include the silencing of the *Arabidopsis* gene APSI a key gene involved in starch biosynthesis (Sanjaya et al., 2011 Plant Biotech J 9:874-883), mutation of CGI-58 (a regulator of neutral lipid accumulation; James et al., 2010 Proc Natl Acad Sci USA 107:17833-17838), and overexpression of mammalian monoacyglycerol acyltransferase in tobacco (*Nicotiana tabacum*) leaves (Petrie et al., 2012 PLOS ONE 7: e35214).

Leaf TAG is used as a short-term storage intermediate of thylakoid lipid during ongoing membrane turnover, remodeling, and senescence. Despite gains in manipulating TAG levels in vegetative tissues (5- to 20-fold in leaves) and microorganisms, it has been acknowledged that to achieve further increases in TAG, preventing its catabolismmay be important (Ohlrogge et al., 2009 Science 324:1019-1020; Slocombe et al., 2009 Plant Biotechnol J 7:694-703; Yang and Ohlrogge, 2009 Plant Physio 1 150:1981-1989; James et al., 2010 Proc Natl Acad Sci USA 107:17833-17838; Troncoso-Ponce et al., 2013 Plant Sci 205-206:13-19). In contrast to leaves and yeast, seeds store TAG as a long-term energy supply by way of a distinctive proteinaceous emulsifier called oleosin that coats the outside of the lipid droplets (LDs; commonly referred to as oil bodies) (Tzen et al., 1992 J Biol Chem 267:15626-15634). Oil bodies (OBs) consist of a TAG core surrounded by a phospholipid monolayer embedded with proteinaceous emulsifiers, 80-90% of which is oleosin. Oleosin prevents the accidental exposure to lipases and inhibits LD coalescence during desiccation, freezing, and germination (Tzen et al., 1992 J Biol Chem 267:15626-15634; Siloto et al., 2006 Plant Cell 18:1961-1974).

An alternative way to stabilize LDs may be to cross link the amphipathic arms of the oleosins (Peng et al., 2003 Biotechnol Prog 19:1623-1626). Polyolesins encoding two or more oleosin repeat units have been described (US 2009/0133160). Coexpression of a combination of genes to enhance TAG production, including wrinkled1 (WRl1), medium chain thioesterase (MCT or T), diacylglycerol acyltrasferase (DGAT) and olesin 1 (Ole1) has been described by Shanklin et al (US 2014/0031573). Various modified DGAT proteins, including chimeric DGAT proteins and N-terminal region modified DGAT have been described and expressed in plants in an effort to increase TAG (for example US 2015/0284726, US 2015/0275223, US 2015/0252378 and US 2011/0191905). Roberts and collaborators have also described modified oleosins with at least one artificially introduced cysteine, particularly including modified oleosin with 6 introduced cysteines, which result in 2-fold and 5-fold increases in the fatty acid content of mature leaves and roots respectively, including when co-expressed with DGAT in Aridopsis (Aridopsis *thaliana*) (Winichayakul S et al (2013) Plant Physiol 162:626-639; US 2012/0278951; U.S. Pat. No. 8,987,551).

The bulk of the world's lipids are produced by plants and the densest form of lipid is as a triacylglycerol (TAG).

Dicotyledonous plants can accumulate up to approximately 60% of their seed weight as TAG which is subsequently used as an energy source for germination. As such there have been a number of efforts targeted at using seeds rich in oils to sustainably produce sufficient lipids for both animal and biofuel feed stock. Upon a single methylation or ethylation step TAG is easily converted to biodiesel which can be used as a transportation fuel or as a feedstock to produce specialty chemicals. To make such processes economically viable, it is critical to optimize yields of TAG in either seeds, or vegetative tissues. Oleosin (also known as OLE1) is an applicable target for overexpression and/or modification to improve energy content and stabilize TAG. While various groups have overexpressed wild type/native OLE1 or mutant forms of OLE1 to increase TAG protection, sometimes with other proteins such as DGAT and WR11, there still is a need for alternative approaches to improve energy content and increase and stabilize triacylglycerol, including in seed and plants. This invention is directed to mutant or variant oleosins and their use and applicability to substantially increase TAG, stabilize TAG and improve energy content in seeds and plants.

The citation of references herein shall not be construed as an admission that such is prior art to the present invention.

SUMMARY OF THE INVENTION

In nature, flowering plants efficiently store energy in their seeds through the accumulation of oil, namely triacylglycerol (TAG), and store it in discreet oil bodies by embedding a phospholipid protein monolayer around the oil body. These seed crops have been used in a variety of agricultural applications as feed and more recently also as a feedstock source for biofuels. On a per weight basis, lipids have approximately double the energy content of either proteins or carbohydrates and as such, substantial focus has been placed on raising the oil content of various species, most notably plants. Unfortunately plant seeds represent a very small percentage of total plant biomass and with the demand for improved agricultural productivity and alternative energies it is recognized that current oil production from a number of devoted seed crops is insufficient. It is therefore a general object of the invention to provide methods for increasing the level of oil production in plant tissues/organs and/or methods for increasing the production of oil from plants.

In accordance with the present invention, variant or mutant oleosin polypeptides are provided wherein one or more amino acid substitution and/or one or more amino acid deletion are introduced.

As used herein "arginine replacement" refers to the one or more amino acid at certain amino acid residue positions in SEQ ID NO:1 being replaced or substituted with or changed or converted to arginine (e.g., lysine is replaced with arginine at certain positions). In other words, the corresponding amino acid at one or more positions is replaced with or mutated to arginine.

The invention thus provides a mutant oleosin (OLE) polypeptide comprising:
 (a) an arginine replacement at one or more amino acid residue selected from positions 27, 105, 117, 119, 123 and 128 in SEQ ID NO:1 or at comparable positions to positions 27, 105, 117, 119, 123 and 128 in SEQ ID NO:1;
 (b) an amino acid deletion at one or more amino acid residue selected from positions 3, 12, 23, 112, 123 and 136 in SEQ ID NO:1 or at comparable positions to positions 3, 12, 23, 112, 123 and 136 in SEQ ID NO:1;
 (c) an arginine replacement at one or more amino acid residue selected from positions 27, 105, 117, 119 and 128 in SEQ ID NO:1 or at comparable positions to positions 27, 105, 117, 119 and 128 in SEQ ID NO:1 and a cysteine replacement at one or more amino acid residue selected from positions 3, 12, 23, 112, 123 and 136 in SEQ ID NO: 1 or at comparable positions to positions 3, 12, 23, 112, 123 and 136 in SEQ ID NO:1; or
 (d) an arginine replacement at one or more amino acid residue selected from positions 27, 105, 117, 119 and 128 in SEQ ID NO:1 or at comparable positions to positions 27, 105, 117, 119 and 128 in SEQ ID NO: 1 and an amino acid deletion at one or more amino acid residue selected from positions 3, 12, 23, 112, 123 and 136 in SEQ ID NO: 1 or at comparable positions to positions 3, 12, 23, 112, 123 and 136 in SEQ ID NO:1.

Native sesame Oleisin1 (OLE1) aa sequence utilized and referenced herein SEQ ID NO: 1 corresponds to the following:
MAEHYGQQQQTRAPHLQLQPRAQRVVKAATA-VTAGGSLLVLSGLTLAGTVIALTIATPLL VIFSPVL-VPAVITI FLLGAGFLASGGFGVAALSVLSWIYRYLTG-KHPPGADQLESAKTKL ASKAREMKDRAEQFS-QOPVAGSQTS In one or more embodiments, the mutant oleosin polypeptide comprises:
 (a) an arginine replacement at amino acid residues at positions 27, 105, 117, 119, 123 and 128 in SEQ ID NO:1 or at comparable positions to positions 27, 105, 117, 119, 123 and 128 in SEQ ID NO:1;
 (b) an amino acid deletion at amino acid residue positions 3, 12, 23, 112, 123 and 136 in SEQ ID NO:1 or at comparable positions to positions 3, 12, 23, 112, 123 and 136 in SEQ ID NO: 1;
 (c) an arginine replacement at amino acid residues positions 27, 105, 117, 119 and 128 in SEQ ID NO:1 or at comparable positions to positions 27, 105, 117, 119 and 128 in SEQ ID NO: 1 and further comprises an amino acid deletion at amino acid residue positions 3, 12, 23, 112, 123 and 136 in SEQ ID NO:1 or at comparable positions to positions 3, 12, 23, 112, 123 and 136 in SEQ ID NO:1;
 (d) an arginine replacement at amino acid residues at positions 27, 105 and 117 in SEQ ID NO: 1 or at comparable positions to positions 27, 105 and 117 in SEQ ID NO:1 and further comprises an amino acid deletion at amino acid residue positions 12 and 123 in SEQ ID NO: 1 or at comparable positions to positions 12 and 123 in SEQ ID NO:1; or
 (e) an arginine replacement at amino acid residue 27 SEQ ID NO:1 or at comparable positions to position 27 in SEQ ID NO:1 and further comprises an amino acid deletion at amino acid residue positions 12 and 123 in SEQ ID NO:1 or at comparable positions to positions 12 and 123 in SEQ ID NO:1.

In particular embodiments of the mutant oleosin polypeptides herein, the mutant oleosin has an amino acid sequence as set out in FIG. 3 or in any one of SEQ ID NOs: 2-19.

In particular embodiments, the mutant oleosin has an amino acid sequence as set out in SEQ ID NO: 6, 7 or 8.

In one embodiment, mutant oleosin having one or more lysine residue replaced with an arginine residue are provided. In one embodiment, six lysine residues in native oleosin polypeptide sequence are replaced with arginine. In one such embodiment, OLE1_KR, such as set out in SEQ ID NO:2, is provided, which is a form of Oleosin where at 6 locations the Lysine was changed to Arginine. The six locations in oleosin polypeptide correspond to each of amino acid positions 27, 105, 117, 119, 123 and 128. Thus, the corresponding lysine amino acid at position 27, 105, 117, 119, 123 and 128, by comparing sequence to Ole1 sequence SEQ ID NO: 1 provided herein (sesame oleosin sequence) is mutated to arginine.

In an embodiment, the corresponding lysine amino acid at one or more of positions 27, 105, 117, 119, 123 and 128, by comparing sequence to Ole1 sequence SEQ ID NO: 1 provided herein (sesame oleosin sequence), is mutated to arginine. In an embodiment, the corresponding lysine amino acid at two or more of positions 27, 105, 117, 119, 123 and 128, by comparing sequence to Ole1 sequence SEQ ID NO: 1 provided herein (sesame oleosin sequence), is mutated to arginine. In an embodiment, the corresponding lysine amino acid at three or more of positions 27, 105, 117, 119, 123 and 128, by comparing sequence to Ole1 sequence SEQ ID NO: 1 provided herein (sesame oleosin sequence), is mutated to arginine. In an embodiment, the corresponding lysine amino acid at four or more of positions amino acid 27, 105, 117, 119, 123 and 128, by comparing sequence to Ole1 sequence SEQ ID NO: 1 provided herein (sesame oleosin sequence), is mutated to arginine. In an embodiment, the corresponding lysine amino acid at five or more of positions amino acid 27, 105, 117, 119, 123 and 128, by comparing sequence to Ole1 sequence SEQ ID NO: 1 provided herein (sesame oleosin sequence), is mutated to arginine. In an aspect, the corresponding lysine amino acid at five positions particularly amino acid 27, 105, 117, 119 and 128, by comparing sequence to Ole1 sequence SEQ ID NO: 1 provided herein (sesame oleosin sequence), is mutated to arginine.

In another embodiment, the invention provides mutant oleosin wherein Lysine is replaced by Arginine, and wherein oleosin sequence is additionally mutated to comprise cysteine amino acid replacements. In one such embodiment, mutant oleosin comprises arginine replacements for lysine at amino acid residues selected from positions 27, 105, 117, 119 and 128, by comparing sequence to Ole1 sequence SEQ ID NO: 1 provided herein (sesame oleosin sequence), and further comprises cysteine amino acid replacements at amino acids selected from positions 3, 12, 23, 112, 123 and 136, by comparing sequence to Ole1 sequence SEQ ID NO: 1 provided herein (sesame oleosin sequence). Notably, in accordance with this embodiment, native lysine amino acid 123 is replaced with cysteine. An exemplary such mutant oleosin is provided in Cys_Ole_KR, such as set out in SEQ ID NO: 4.

In one embodiment, mutant oleosin comprises arginine replacements for lysine at each of amino acid residues 27, 105, 117, 119 and 128, by comparing sequence to Ole1 sequence SEQ ID NO: 1 provided herein (sesame oleosin sequence), and further comprises cysteine amino acid replacements at amino acids 3, 12, 23, 112, 123 and 136, by comparing sequence to Ole1 sequence SEQ ID NO: 1 provided herein (sesame oleosin sequence). In one such embodiment, exemplary mutant oleosin designated Cys_OLE1_KR comprises cysteine mutations at each of amino acids 3, 12, 23, 112, 123 and 136 and further comprises arginine at amino acids 27, 105, 117, 119 and 128.

In an embodiment of the invention, mutant oleosin is provided comprising one or more arginine replacements at amino acid residues selected from positions 27, 105, 117, 119, 123 and 128, by comparing sequence to Ole1 sequence SEQ ID NO: 1 provided herein (sesame oleosin sequence), and further comprising one or more cysteine amino acid replacements at amino acids selected from positions 3, 12, 23, 112, 123 and 136, by comparing sequence to Ole1 sequence SEQ ID NO: 1 provided herein (sesame oleosin sequence).

In another embodiment, mutant oleosin is provided having amino acids deleted. In one such aspect, amino acids at one or more of or at all of corresponding positions of amino acids 3, 12, 23, 112, 123 and 136, by comparing sequence to Ole1 sequence SEQ ID NO: 1 provided herein (sesame oleosin sequence) are deleted. In exemplary mutant oleosin designated OLE1_Cys_DEL, such as set out in SEQ ID NO:5, a mutant oleosin is provided wherein 6 amino acid residues at positions corresponding to amino acids 3, 13, 23, 112, 123 and 136 are deleted. In the native oleosin sequence provided herein designated OLE1 (SEQ ID NO:1) each of the amino acids E at 3, R at 12, Q at 23, Q at 112, K at 123 and Q at 136 are removed or deleted.

In an embodiment, the invention provides an oleosin mutant comprising amino acid mutations and amino acid deletions. This embodiment thus comprises certain of the mutant oleosin aspects in combination. In one such embodiment, a mutant oleosin is provided combining all amino acid replacement and deletion aspects as detailed above. In an exemplary such mutant oleosin having combined replacements and deletions, designated OLE1_Cys_DEL_KR, such as set out in SEQ ID NO: 6, the native lysine was changed to arginine at five locations namely amino acids 27, 105, 117, 119 and 128 and 6 amino acid residues were deleted at positions corresponding to amino acids 3, 13, 23, 112, 123 and 136 (E at 3, R at 12, Q at 23, K at 27, Q at 112, K at 123 and Q at 136 in SEQ ID NO:1).

In another embodiment, mutant oleosin is provided comprising an arginine replacement at amino acid residues at positions 27, 105 and 117 in SEQ ID NO:1 and further comprising an amino acid deletion at amino acid residue positions 12 and 123 in SEQ ID NO:1. The mutant is designated Ole1_5mod. Ole1_5mod is exemplified in the mutant polypeptide sequence as set out in SEQ ID NO:7.

In another embodiment, mutant oleosin is provided comprising an arginine replacement at amino acid residue 27 SEQ ID NO: 1 and further comprising an amino acid deletion at amino acid residue positions 12 and 123 in SEQ ID NO:1. The mutant is designated Ole1_3mod. Ole1_3mod is exemplified in the mutant polypeptide sequence as set out in SEQ ID NO:8.

In other embodiments, mutant oleosins combining one or more arginine amino acid replacement selected from positions 27, 105, 117, 119, 123 and 128, by comparing sequence to Ole1 sequence SEQ ID NO: 1 provided herein (sesame oleosin sequence), and one or more amino acid deletions at amino acids selected from positions 3, 12, 23, 112, 123 and 136, by comparing sequence to Ole1 sequence SEQ ID NO: 1 provided herein (sesame oleosin sequence) are provided. In such embodiments, mutant oleosins combining up to five arginine amino acid replacements selected from positions 27, 105, 117, 119 and 128 and up to six amino acid deletions at amino acids selected from positions 3, 12, 23, 112, 123 and 136, by comparing sequence to Ole1 sequence SEQ ID NO: 1 provided herein (sesame oleosin sequence) are provided.

Expression of the mutant oleosins allows for the creation of stable oil bodies beyond the reproductive tissue of vascular plants into new cell types and even other species. In an aspect, when combined with a TAG synthesizing enzyme, the invention leads to the accumulation and storage of TAG in cells, or in plants or seeds, as stable oil bodies. Compared with an unmodified cell or plant or even one expressing TAG synthesis enzyme and not expressing mutant oleosin(s) as provided herein, the invention allows for the accumulation of TAG in excess levels when compared to TAG accumulation in native or wild type conditions or genetic backgrounds.

In an additional embodiment of the invention, the mutant oleosin(s) can also be fused to a protein of interest, to form a fusion protein. The fusion protein (mutant oleosin plus protein of interest) can be recombinantly expressed in a cell or organism or plant. In this way oil bodies containing the expressed fusion proteins can be used to purify and deliver the protein of interest, for a variety of applications. In a further embodiment, the mutant oleosin(s) may be labeled, including by attachment to a detectable or functional label.

Nucleic acids or polynucelotides encoding the mutant or variant oleosin polypeptides are also provided. In an embodiment, nucleic acid is provided encoding one or more mutant oleosin as described herein, including mutant oleosin having one or more arginine replacement and one or more amino acid deletion as provided herein. In an embodiment, nucleic acid is provided encoding one or more mutant oleosin as described herein, including mutant oleosin having one or more arginine replacement and one or more cysteine replacement and/or amino acid deletion as provided herein.

In a further embodiment the polynucleotide encodes a fusion protein including the modified oleosin fused to a protein of interest.

In a further embodiment the invention provides an expression construct comprising a polynucleotide of the invention. In one embodiment the polynucleotide in the construct is operably linked to a promoter sequence. In one embodiment the promoter sequence is capable of driving expression of the polynucleotide in a vegetative tissue of a plant. In another embodiment the promoter sequence is capable of driving expression of the polynucleotide in a seed of a plant. In a further embodiment the promoter sequence is capable of driving expression of the polynucleotide in the pollen of a plant. In a further embodiment the promoter sequence is capable of driving expression of the polynucleotide in a bacterial cell or yeast cell.

In another embodiment, the invention provides a construct containing a polynucleotide that encodes a mutant oleosin as provided herein. In one embodiment, the construct also contains a second polynucleotide that encodes a triacylglycerol (TAG) synthesizing enzyme. In various embodiments, the construct can be linked to a promoter sequence capable of driving its expression in various host cells. As such, the invention also provides use of the constructs to induce a host cell to express a modified oleosin and/or protein components including enzymes and transcription factors that modulate TAG synthesis. In various embodiments, the construct expressing a mutant oleosin and the construct expressing a TAG synthesizing enzyme may be driven by the same or by different promoters. In yet another embodiment the construct is located in an appropriate position and orientation of a suitable functional endogenous promoter such that the expression of the construct occurs. In various embodiments, the construct can be expressed in a bacterial, plant, fungal or algal cell. In one embodiment where the construct is expressed in a plant cell, the cell may be of vegetative, seed, pollen or fruit tissue.

In another embodiment, the invention provides a host cell comprising a construct and mutant oleosin of the invention. In an embodiment the invention provides a host cell genetically modified to comprise a polynucleotide of the invention. In a further embodiment the invention provides a host cell genetically modified to express a polynucleotide of the invention.

In a further embodiment the host cell is also genetically modified to express a triacylglycerol (TAG) synthesizing enzyme. In one such embodiment, the host cell is genetically modified to comprise a nucleic acid sequence encoding a triacylglycerol (TAG) synthesizing enzyme. In another embodiment the host cell comprises an expression construct including a nucleic acid sequence encoding a triacylglycerol (TAG) synthesizing enzyme.

In a further embodiment the nucleic acid is operably linked to a promoter sequence. The promoter sequence may capable of driving expression of the nucleic acid sequence in a vegetative tissue of a plant. In one aspect the promoter sequence is capable of driving expression of the nucleic acid sequence in a seed of a plant or in the pollen of a plant. The promoter sequence may be capable of driving expression of the polynucleotide in a bacterial cell or in a yeast cell.

The host cell may be any suitable type of cell, including a prokaryotic cell or a eukaryotic cell. In one embodiment the host cell is selected from a bacterial cell, a yeast cell, a fungal cell, an insect cell, algal cell, and a plant cell. In a particular embodiment the host cell is a plant cell.

The invention further provides a plant comprising a plant cell of the invention. In one aspect the invention provides a plant comprising a construct of the invention. In an aspect the invention provides a plant genetically modified to comprise or to express a polynucleotide of the invention. In a further embodiment the plant expresses a mutant oleosin provided herein and encoded by the polynucleotide or nucleic acid of the invention.

In a further a embodiment, the plant is also genetically modified to express a triacylglycerol (TAG) synthesizing enzyme. In a further embodiment the triacylglycerol (TAG) synthesizing enzyme is expressed in the same tissue as the modified oleosin. In a further embodiment the plant is genetically modified to comprise a nucleic acid sequence encoding a triacylglycerol (TAG) synthesizing enzyme. In a further embodiment the plant comprises an expression construct including a nucleic acid sequence encoding a triacylglycerol (TAG) synthesizing enzyme. In another aspect the plant may be genetically modified to express or overexpress DGAT2 and/or WRI1.

The nucleic acid or polynucleotide of the invention may be operably linked to a promoter sequence. In an aspect, the promoter is suitable and applicable for expression in plants. In an aspect, the promoter is a constitutive promoter. In an aspect, the promoter is an inducible promoter. In an aspect, the promoter is a plant specific promoter, or a promoter directing expression in leaves, tissues or seeds of a plant. In an aspect, the promoter sequence is capable of driving expression of the nucleic acid sequence in a vegetative tissue of a plant. In one embodiment the promoter sequence is capable of driving expression of the nucleic acid sequence in a seed of a plant. In one embodiment the promoter sequence is capable of driving expression of the nucleic acid sequence in the pollen of a plant. In embodiments, the promoter may be the constitutive promoter 35S or may be a seed promoter, particularly a strong seed promoter such as the promoter for the gene phaseolin.

In a further embodiment the invention provides an oil body comprising a mutant oleosin, or one or more mutant oleosin(s) of the invention. In a further embodiment the invention provides an oil body comprising at least two mutant oleosins of the invention. In one embodiment at least two of the modified oleosins are cross-linked to each other, such as via disulphide bridges and cysteine residues.

In a further embodiment the invention provides a composition comprising a mutant oleosin of the invention. In one embodiment the composition comprises the mutant oleosin and a suitable carrier.

The mutant oleosins may be modified naturally occurring oleosins. The plants from which the un-modified or naturally occurring oleosin sequences are derived may be from any plant species that contains oleosins and polynucleotide sequences encoding oleosins. The plant cells in which the mutant oleosins are expressed may be from any plant species. The plants in which the mutant oleosins are expressed may be from any plant species. In one embodiment the plant cell or plant, is derived from a gymnosperm plant species. In a further embodiment the plant cell or plant, is derived from an angiosperm plant species. In a further embodiment the plant cell or plant, is derived from a from dicotyledonous plant species. In a further embodiment the plant cell or plant, is derived from a monocotyledonous plant species. The plant or plant cell may be sugar cane, sorghum or other bioenergy crop. The plant or plant cell may be a non-bioenergy crop.

In one embodiment the plant accumulates more total lipid in its non-photosynthetic tissues/organs than does a control plant. In a further embodiment the plant accumulates at least 10%, more preferably at least 20%, more preferably at least 50%, more preferably at least 100%, more preferably 150%, more preferably 200%, more preferably 250%, more preferably 300%, more preferably 350%, more preferably 400%, more preferably 450%, more preferably 500%, more total lipid in its non-photosynthetic tissues/organs than does a control plant. In one embodiment the plant produces total lipid in its non-photosynthetic tissues/organs in the range 100% to 900%, more preferably 200% to 800%, more preferably 300% to 700%, more preferably 400% to 600%, more than a control plant.

Suitable control plants include non-transformed or wild-type versions of plant of the same variety and/or species as the transformed plant used in the method of the invention. Suitable control plants also include plants of the same variety and or species as the transformed plant that are transformed with a control construct. Suitable control plants also include plants that have not been transformed with a polynucleotide encoding a mutant oleosin provided herein. Suitable control plants also include plants that do not express a mutant oleosin provided herein.

Other objects and advantages will become apparent to those skilled in the art from a review of the following description which proceeds with reference to the following illustrative drawings.

BRIEF DESCRIPTION OF THE DRAWINGS

FIG. 3 provides a sequence alignment of native sesame OLE1 (SEQ ID NO: 1) and mutants/variants described herein. Mutants oleosin polypeptides provided are as follows:

| | |
|---|---|
| OLE_KR | (SEQ ID NO: 2) |
| Cys_OLE1 | (SEQ ID NO: 3) |
| Cys_OLE1_KR | (SEQ ID NO: 4) |
| OLE1_Cys_DEL | (SEQ ID NO: 5) |
| OLE1_Cys_DEL KR | (SEQ ID NO: 6) |
| Ole1_5mod | (SEQ ID NO: 7) |
| Ole1_3mod | (SEQ ID NO: 8) |
| OleNative3 | (SEQ ID NO: 9) |
| OleNative12 | (SEQ ID NO: 10) |
| OleNative23 | (SEQ ID NO: 11) |
| OleNative112 | (SEQ ID NO: 12) |
| OleNative123 | (SEQ ID NO: 13) |
| OleNative136 | (SEQ ID NO: 14) |
| OleK27 | (SEQ ID NO: 15) |
| OleK105 | (SEQ ID NO: 16) |
| OleK117 | (SEQ ID NO: 17) |

| | | (SEQ ID NO: 18) |
|---|---|---|
| OleK119 | | |
| | | (SEQ ID NO: 19) |
| OleK128 | | |

Each of positions 3, 12, 23, 112, 123 and 136 in native OLE1 are noted and indicated with a Δ above the amino acid location, indicating that these amino acids are substituted with a cysteine (C) or are deleted (–) in certain oleosin variants. Native lysine residues at each of positions 27, 105, 117, 119, 123 and 128 in native OLE1 are marked with an R above the amino acid location, indicating that these amino acids are substituted with an arginine (R) in certain oleosin variants.

FIG. 4 provides an alignment of available and known oleosin sequences from various plants. The corresponding location of the deletions (denoted 4) and the Lys to Arg mutations (denoted R*) in the native Ole sequence are indicated. The first sequence denoted Ole1 BNL is the wild type oleosin sesame sequence utilized herein (SEQ ID NO:1). The alternative oleosin sequences correspond to publicly available sequences as follows: Ole *Sesamum* (SEQ ID NO:20)—*Sesame indicum* (alternative sesame) sequence, Accession No ACH85188.1; Ole Citrus (SEQ ID NO:21)—corresponds to *Citrus clementina* sequence (clementine), Accession No XP_006421522 (sequence also corresponds to *Citrus sinensis* sequence (sweet orange, navel orange, blood orange) Accession No XP_006490018, and to Citrus unshiu sequence (cold hardy mandarine) Accesssion No GAY55630; Ole *Nicotiana* (SEQ ID NO:22)—tobacco *Nicotiana sylvestris* sequence Accession No XP_009778273 (sequence also corresponds to *Nicotiana tomentosiformis* sequence Accession No XP_009601962); Ole Punica (SEQ ID NO: 23)—Punica granatum sequence (pomegranate) Accession No. XP_031379163).

Figure 5:
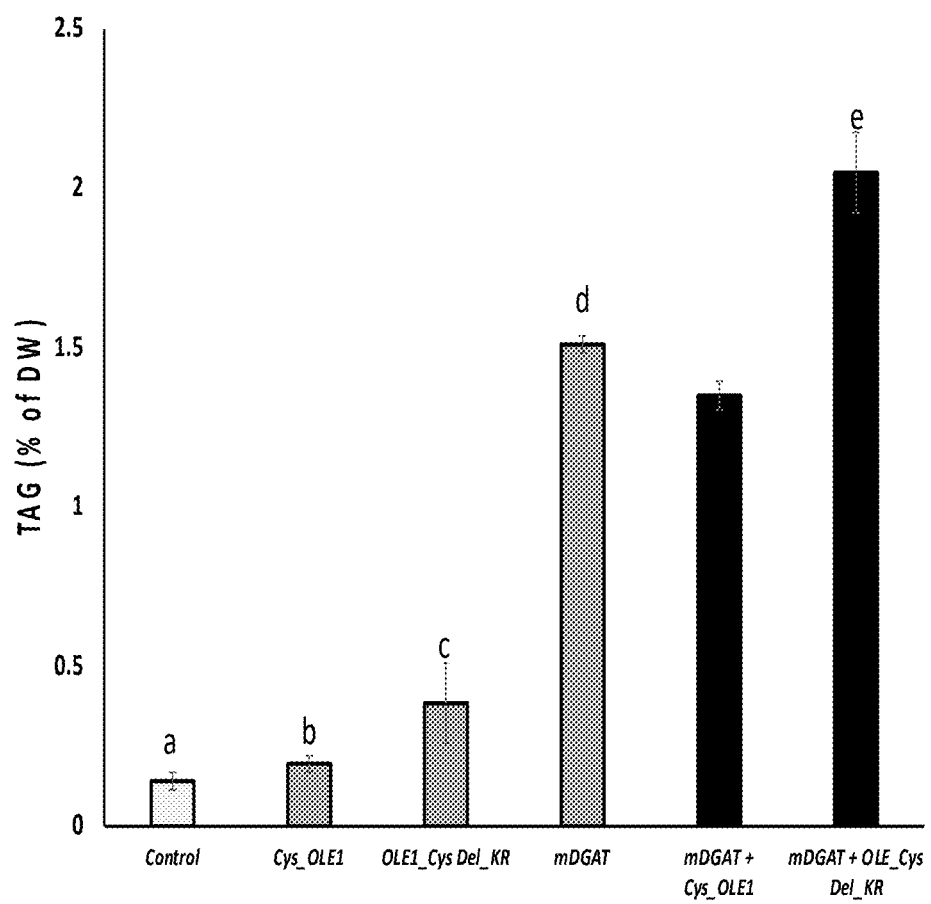

FIG. 5 depicts co-expression of OLE_Cys DEL_KR and mouse DGAT (mDGAT) resulted in higher TAG accumulation in *N. bethamiana* leaves. TAG content was quantitated upon transiently co-expressing OLE_CysDEL_KR and mDGAT, and was compared with co-expression of Cys_OLE1 and mDGAT. Data represents average of at least 4 biological replicates±SD. A T-test was performed to determine the significance.

FIG. 6 depicts co-expression of OLE_Cys DEL_KR variant of sesame oleosin produces the most significant increase in both total fatty acid and TAG content in *Arabidopsis* seeds. All the oleosin variants were driven by a seed specific phaseolin promoter and tagged by DS red dye. (A) TFA content. (B) TAG content. Data represents average of at least 3 overexpression lines±SD. A T-test was performed to determine the significance with WT.

FIG. 7 depicts contribution of individual amino acid modification in OLE_Cys DEL_KR towards TAG accumulation. Each number represents the position of amino acid (aa) that was substituted from OLE_Cys DEL_KR to the aa present in native oleosin. TAG content was quantified upon transiently expressing Oleosin variants in *N. bethamiana* leaves. (A) in place of an aa deletion (Del) in OLE_Cys DEL_KR a corresponding aa from native oleosin was inserted. (B) in place of an arginine in OLE_Cys DEL_KR a corresponding lysine was substituted.

FIG. 8 depicts oleosin variant with 5 modifications (Ole1_5 Mod) resulted in most significant increase in TAG accumulation. (A) TAG content was quantified upon transiently expressing the oleosin variants in *N. bethamiana* leaves. (B) TAG content was quantified upon transiently co-expressing the oleosin variants with a mDGAT. Data represents average of at least 4 biological replicates±SD. A T-test was performed to determine the statistical significance.

DETAILED DESCRIPTION

In accordance with the present invention there may be employed conventional molecular biology, microbiology, and recombinant DNA techniques within the skill of the art.

Therefore, if appearing herein, the following terms shall have the definitions set out below.

The terms "mutant oleosin", "variant oleosin", "mutant oleosins", variant oleosins" and any variants not specifically listed, may be used herein interchangeably, and as used throughout the present application and claims refer to polypeptides and proteinaceous material including single or multiple proteins, and extends to those proteins having the amino acid sequence data described herein and presented in FIG. 3 and the sequences as described herein including in SEQ ID NOs: 2-19, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "mutant oleosin", "variant oleosin", "mutant oleosins", variant oleosins" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | AMINO |
| 1-Letter | 3-Letter | ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |

-continued

TABLE OF CORRESPONDENCE

| SYMBOL | | AMINO ACID |
|---|---|---|
| 1-Letter | 3-Letter | |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "probe" refers to a short polynucleotide that is used to detect a polynucleotide sequence that is complementary to the probe, in a hybridization-based assay. The probe may consist of a "fragment" of a polynucleotide as defined herein.

The term "primer" as used herein refers to a short polynucleotide, usually having a free 3'OH group, that is hybridized to a template and used for priming polymerization of a polynucleotide complementary to the target. A "primer" may be an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis.

A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. It should be appreciated that also within the scope of the present invention are DNA sequences encoding which code for a having the same amino acid sequence as SEQ ID NO:, but which are degenerate to SEQ ID NO:. By "degenerate to" is meant that a different three-letter codon is used to specify a particular amino acid. It is well known in the art that the following codons can be used interchangeably to code for each specific amino acid:

Phenylalanine (Phe or F) UUU or UUC
Leucine (Leu or L) UUA or UUG or CUU or CUC or CUA or CUG
AUU or AUC or AUA Isoleucine (Ile or I)
Methionine (Met or M) AUG
Valine (Val or V) GUU or GUC of GUA or GUG
Serine (Ser or S) UCU or UCC or UCA or UCG or AGU or AGC
Proline (Pro or P) CCU or CCC or CCA or CCG
Threonine (Thr or T) ACU or ACC or ACA or ACG
Alanine (Ala or A) GCU or GCG or GCA or GCG
Tyrosine (Tyr or Y) UAU or UAC
Histidine (His or H) CAU or CAC
Glutamine (Gln or Q) CAA or CAG
Asparagine (Asn or N) AAU or AAC
Lysine (Lys or K) AAA or AAG
Aspartic Acid (Asp or D) GAU or GAC
Glutamic Acid (Glu or E) GAA or GAG
Cysteine (Cys or C) UGU or UGC
Arginine (Arg or R) CGU or CGC or CGA or CGG or AGA or AGG
Glycine (Gly or G) GGU or GGC or GGA or GGG
Tryptophan (Trp or W) UGG
Termination codon UAA (ochre) or UAG (amber) or UGA (opal)

It should be understood that the codons specified above are for RNA sequences. The corresponding codons for DNA have a T substituted for U.

Mutations can be made in oleosin sequence including in SEQ ID NO:1 as provided herein such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping).

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined $T_m$ with washes of higher stringency, if desired.

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 25 nucleotides, more preferably at least 30 nucleotides, more preferably at least 35 nucleotides, more preferably at least 40 nucleotides, more preferably at least 45 nucleotides, more preferably at least 50 nucleotides, more preferably at least 60 nucleotides, more preferably at least 70 nucleotides, more preferably at least 80 nucleotides, more preferably at least 90 nucleotides, more preferably at least 100 nucleotides, more preferably at least 150 nucleotides, more preferably at least 200 nucleotides, more preferably at least 250 nucleotides, more preferably at least 300 nucleotides, more preferably at least 350 nucleotides, more preferably at least 400 nucleotides, more preferably at least 450 nucleotides and most preferably at least 500 nucleotides of contiguous nucleotides of a polynucleotide disclosed. A fragment of a polynucleotide sequence can be used in antisense, RNA interference (RNAi), gene silencing, triple helix or ribozyme technology, or as a primer, a probe, included in a microarray, or used in polynucleotide-based selection methods of the invention.

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/).

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/).

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

The term "variant" with reference to polypeptides encompasses recombinantly and synthetically produced polypeptides. Variant polypeptide sequences preferably exhibit at least 50%, more preferably at least 60%, more preferably at least 70%, more preferably at least 75%, more preferably at least 80%, more preferably at least 85%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention. Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ncbi.nih.gov/blast).

Polypeptide variants of the present invention, or used in the methods of the invention, also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/).

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction: a) a promoter functional in the host cell into which the construct will be transformed, b) the polynucleotide to be expressed, and c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence may, in some cases, identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

As used herein, "pg" means picogram, "ng" means nanogram, "ug" or "μg" mean microgram, "mg" means milligram, "ul" or "μl" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage 2, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, promoters. Promoters suitable for expression in plants are well known and available. A tissue/organ preferred promoter is a promoter that drives expression of an operably linked polynucleotide in a particular tissue/organ at a higher level than in other tissues/organs. A tissue specific promoter is a promoter that drives expression of an operably linked polynucleotide specifically in a particular tissue/organ. Even with tissue/organ specific promoters, there is usually a small amount of expression in at least one other tissue. A tissue specific promoter is by definition also a tissue preferred promoter. Vegetative Tissue Specific Promoters—An example of a vegetative specific promoter is found in U.S. Pat. Nos. 6,229,067; and 7,629,454; and 7,153,953; and 6,228,643. Pollen Specific Promoters—An example of a pollen specific promoter is found in U.S. Pat. Nos. 7,141,424; and 5,545,546; and 5,412,085; and 5,086,169; and 7,667,097. Seed Specific Promoters—An example of a seed specific promoter is found in U.S. Pat. Nos. 6,342,657; and 7,081,565; and 7,405,345; and 7,642,346; and 7,371,928. Fruit Specific Promoters—An example of a fruit specific promoter is found in U.S. Pat. Nos. 5,536,653; and 6,127,179; and 5,608,150; and 4,943,674. Non-Photosynthetic Tissue Preferred Promoters—Non-photosynthetic tissue preferred promoters include those preferentially expressed in non-photosynthetic tissues/organs of the plant. Non-photosynthetic tissue preferred promoters may also include light repressed promoters. Light Repressed Promoters—An example of a light repressed promoter is found in U.S. Pat. Nos. 5,639,952 and in 5,656,496. Root Specific Promoters—An example of a root specific promoter is found in U.S. Pat. No. 5,837,848; and US 2004/0067506 and US 2001/0047525. Tuber Specific Promoters—An example of a tuber specific promoter is found in U.S. Pat. No. 6,184,443. Bulb Specific Promoters—An example of a bulb specific promoter is found in Smeets et al., (1997) Plant Physiol. 113:765-771. Rhizome Preferred Promoters—An example of a rhizome preferred promoter is found Seong Jang et al., (2006) Plant Physiol. 142:1148-1159. Endosperm Specific Promoters—An example of an endosperm specific promoter is found in U.S. Pat. No. 7,745,697. Photosynthetic Tissue Preferred Promoters—Photosynthetic tissue preferred promoters include those that are preferentially expressed in photosynthetic tissues of the plants. Photosynthetic tissues of the plant include leaves, stems, shoots and above ground parts of the plant. Photosynthetic tissue preferred promoters include light regulated promoters. Light Regulated Promoters—Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, insect cells, and human cells and plant cells in tissue culture. Host cells may be derived from, for example, bacterial, fungal, yeast, insect, mammalian, algal or plant organisms. Host cells may also be synthetic cells. Preferred host cells are eukaryotic cells. A particularly preferred host cell is a plant cell, particularly a plant cell in a vegetative tissue of a plant.

A "transgenic plant" refers to a plant which contains new genetic material as a result of genetic manipulation or transformation. The new genetic material may be derived from a plant of the same species as the resulting transgenic plant or from a different species.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

The labels most commonly employed for studies with relevance to the present invention are known to one skilled in the art. Examples are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The mutant oleosin can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Oleosins are comparatively small (15 to 24 kDa) proteins which allow the oil bodies (OBs) to become tightly packed discrete organelles without coalescing as the cells desiccate or undergo freezing conditions (Leprince et al., 1998; Siloto et al., 2006; Slack et al., 1980; Shimada et al. 2008). The properties of the major oleosins is relatively conserved between plants and oleosin is characterized as a 15-25 kDa protein corresponding to approximately 140-230 amino acid residues. The protein sequence can be divided almost equally along its length into 4 parts which correspond to a N-terminal hydrophilic region, two centre hydrophobic regions (joined by a proline knot or knob) and a C-terminal hydrophilic region. The topology of oleosin is attributed to its physical properties which includes a folded hydrophobic core flanked by hydrophilic domains. This arrangement confers an amphipathic nature to oleosin resulting in the hydrophobic domain being embedded in the phospholipid monolayer (Tzen et al., 1992) while the flanking hydrophilic domains are exposed to the aqueous environment of the cytoplasm.

Examples of oleosin sequences suitable to be mutated as described herein and for use in the invention are well known and available to one skilled in the art including in public sequence databases. For example, a BLAST search of the NCBI sequence protein database with the native OLE1 (SEQ ID NO:1) provided herein will result in numerous related plant oleosin sequences being generated as search output and having sequence identity ranging from 100% to about 60%. Various related or distinct plant species oleosin proteins are therefore known and available. Exemplary sequences from other plants can readily be identified and compared or aligned with the native oleosin OLE1 SEQ ID NO:1 hereof so as to provide comparable corresponding amino acids to generate further or alternative mutant oleosins in accordance with the invention. An example of one such alignment with comparable sequences and target residues for mutation is provided herein for example in FIG. 4.

Alignment of any one or more related plant oleosin sequence(s) with the native oleosin sequence provided herein SEQ ID NO:1, which is well within the knowledge and capability of one skilled in the art, including as exemplified and demonstrated in FIG. 4, provides one with comparable corresponding amino acids in any such one or more related plant oleosin sequence(s) with the sequence of SEQ ID NO:1. These provide comparable positions to positions in SEQ ID NO:1. In accordance with the invention, such alignment or comparison of another plant oleosin or related plant oleosin sequence provides comparable positions in such another plant oleosin or related plant oleosin sequence to positions in SEQ ID NO:1, which are suitable and applicable for generating variants or mutants in line with and in accordance with the present invention. Thus, corresponding amino acid at one or more of position 3, 12, 23, 112, 123 and 136 in SEQ ID NO:1 or comparable amino acids at one or more of position 27, 105, 117, 119, 123 and 128 in SEQ ID NO: 1, etc can be readily determined and identified, including by sequence comparison and/or alignment with SEQ ID NO:1.

With regard to triacylglycerol biosynthesis the only committed step in TAG biosynthesis is the last one, i.e. the addition of a third fatty acid to an existing diacylglycerol, thus generating TAG. In plants this step is predominantly (but not exclusively) performed by one of five (predominantly ER localized) TAG synthesizing enzymes including: acyl CoA: diacylglycerol acyltransferase (DGAT1); an unrelated acyl CoA: diacylglycerol acyl transferase (DGAT2); a soluble DGAT (DGAT3) which has less than 10% identity with DGAT1 or DGAT2 (Saha et al., 2006); phosphatidylcholine-sterol O-acyltransferase (PDAT); and a wax synthase (WSD1, Li et al., 2008). The DGAT1 and DGAT2 proteins are encoded by two distinct gene families, with DGAT1 containing approximately 500 amino acids and 10 predicted transmembrane domains and DGAT2 has only 320 amino acids and two transmembrane domains (Shockey et al., 2006).

The term "triacylglycerol synthesizing enzyme" or "TAG synthesizing enzyme" as used herein means an enzyme capable of catalyzing the addition of a third fatty acid to an existing diacylglycerol, thus generating TAG. Preferred TAG synthesizing enzymes include but are not limited to: acyl CoA: diacylglycerol acyltransferase) (DGAT1); diacylglycerol acyl transferase2 (DGAT2); phosphatidylcholine-sterol O-acyltransferase (PDAT) and cytosolic soluble form of DGAT (soluble DGAT or DGAT3).

Most attempts to date to accumulate TAG in leaves have predominantly focused on three particular gene candidates including over expression of DGAT (TAG biosynthesis), mutation of TGD1 or CTS (resulting in the prevention of lipid remobilization), and over expression of LEC1, LEC2 and WRI1 (transcriptional factors involved in storage oil and protein accumulation in developing seeds). Over expression of TAG and other neutral lipid synthesizing enzymes relies on the presence of sufficient substrate, in the expanding and or mature leaf this is assumed to be provided by the plastid (chloroplast in the case of the leaf) which synthesizes lipids for membranes. In photosynthetic leaves of *Arabidopsis* it has been estimated that the turnover of membrane lipids is 4% of total fatty acids per day (Bao et al, 2000). In senescing leaves, the existing plastidal membranes provide the bulk of fatty acids for partitioning into TAG prior to further mobilization.

In a most general aspect of the invention, variant or mutant oleosin polypeptides are provided wherein one or more amino acid substitution and/or one or more amino acid deletion are introduced.

As used herein "arginine replacement" refers to the one or more amino acid at certain amino acid residue positions in SEQ ID NO:1 being replaced or substituted with or changed or converted to arginine (e.g., lysine is replaced with arginine at certain positions). In other words, the corresponding amino acid at one or more positions is replaced with or mutated to arginine.

The invention thus provides a mutant oleosin (OLE) polypeptide comprising:
(a) an arginine replacement at one or more amino acid residue selected from positions 27, 105, 117, 119, 123 and 128 in SEQ ID NO: 1 or at comparable positions to positions 27, 105, 117, 119, 123 and 128 in SEQ ID NO:1;
(b) an amino acid deletion at one or more amino acid residue selected from positions 3, 12, 23, 112, 123 and 136 in SEQ ID NO: 1 or at comparable positions to positions 3, 12, 23, 112, 123 and 136 in SEQ ID NO:1;
(c) an arginine replacement at one or more amino acid residue selected from positions 27, 105, 117, 119 and 128 in SEQ ID NO: 1 or at comparable positions to positions 27, 105, 117, 119 and 128 in SEQ ID NO: 1 and a cysteine replacement at one or more amino acid residue selected from positions 3, 12, 23, 112, 123 and 136 in SEQ ID NO:1 or at comparable positions to positions 3, 12, 23, 112, 123 and 136 in SEQ ID NO:1; or
(d) an arginine replacement at one or more amino acid residue selected from positions 27, 105, 117, 119 and 128 in SEQ ID NO: 1 or at comparable positions to positions 27, 105, 117, 119 and 128 in SEQ ID NO: 1 and an amino acid deletion at one or more amino acid residue selected from positions 3, 12, 23, 112, 123 and 136 in SEQ ID NO: 1 or at comparable positions to positions 3, 12, 23, 112, 123 and 136 in SEQ ID NO:1.

In one or more embodiments, the mutant oleosin polypeptide comprises:
(a) an arginine replacement at amino acid residues at positions 27, 105, 117, 119, 123 and 128 in SEQ ID NO:1 or at comparable positions to positions 27, 105, 117, 119, 123 and 128 in SEQ ID NO:1;
(b) an amino acid deletion at amino acid residue positions 3, 12, 23, 112, 123 and 136 in SEQ ID NO:1 or at comparable positions to positions 3, 12, 23, 112, 123 and 136 in SEQ ID NO: 1;
(c) an arginine replacement at amino acid residues positions 27, 105, 117, 119 and 128 in SEQ ID NO:1 or at comparable positions to positions 27, 105, 117, 119 and 128 in SEQ ID NO: 1 and further comprises an amino acid deletion at amino acid residue positions 3, 12, 23, 112, 123 and 136 in SEQ ID NO:1 or at comparable positions to positions 3, 12, 23, 112, 123 and 136 in SEQ ID NO:1;
(d) an arginine replacement at amino acid residues at positions 27, 105 and 117 in SEQ ID NO: 1 or at comparable positions to positions 27, 105 and 117 in SEQ ID NO: 1 and further comprises an amino acid deletion at amino acid residue positions 12 and 123 in SEQ ID NO: 1 or at comparable positions to positions 12 and 123 in SEQ ID NO:1; or
(e) an arginine replacement at amino acid residue 27 SEQ ID NO:1 or at comparable positions to position 27 in SEQ ID NO:1 and further comprises an amino acid deletion at amino acid residue positions 12 and 123 in SEQ ID NO:1 or at comparable positions to positions 12 and 123 in SEQ ID NO:1.

In particular embodiments of the mutant oleosin polypeptides herein, the mutant oleosin has an amino acid sequence as set out in FIG. 3 or in any one of SEQ ID NOs: 2-19.

In particular embodiments, the mutant oleosin has an amino acid sequence as set out in SEQ ID NO: 6, 7 or 8.

Mutant oleosin(s) having one or more lysine residue replaced with an arginine residue are provided. In one aspect, six lysine residues in native oleosin polypeptide sequence are replaced with arginine. OLE1_KR is provided as one such exemplary mutant oleosin (exemplified in SEQ ID NO:2), which is a form of Oleosin where at 6 locations the lysine was changed to arginine. The six locations in oleosin polypeptide correspond to each of amino acid positions 27, 105, 117, 119, 123 and 128. Thus, the corresponding lysine amino acid at position 27, 105, 117, 119, 123 and 128, by comparing sequence to Ole1 sequence SEQ ID NO: 1 provided herein (sesame oleosin sequence) is mutated to arginine.

Mutant oleosin(s) are provided wherein the corresponding lysine amino acid at one or more of positions 27, 105, 117, 119, 123 and 128, by comparing sequence to Ole1 sequence SEQ ID NO: 1 provided herein (sesame oleosin sequence), is mutated to arginine. In an aspect, the corresponding lysine amino acid at two or more of positions 27, 105, 117, 119, 123 and 128, by comparing sequence to Ole1 sequence SEQ ID NO: 1 provided herein (sesame oleosin sequence), is mutated to arginine. In an embodiment, the corresponding lysine amino acid at three or more of positions 27, 105, 117, 119, 123 and 128, by comparing sequence to Ole1 sequence SEQ ID NO: 1 provided herein, is mutated to arginine. In an aspect, the corresponding lysine amino acid at four or more of positions amino acid 27, 105, 117, 119, 123 and 128, by comparing sequence to Ole1 sequence SEQ ID NO: 1 provided herein, is mutated to arginine. In an embodiment, the corresponding lysine amino acid at five or more of positions amino acid 27, 105, 117, 119, 123 and 128, by comparing sequence to Ole1 sequence SEQ ID NO: 1 provided herein, is mutated to arginine. In an embodiment, the corresponding lysine amino acid at five positions particularly amino acid 27, 105, 117, 119 and 128, by comparing sequence to Ole1 sequence SEQ ID NO: 1 provided herein, is mutated to arginine. One such embodiment is Ole_KR as described herein and in FIG. 3 and in corresponding to SEQ ID NO:2.

In another aspect, the invention provides mutant oleosin wherein lysine is replaced by arginine, and wherein oleosin sequence is additionally mutated to comprise cysteine amino acid replacements. In one such aspect, mutant oleosin comprises arginine replacements for lysine at amino acid residues selected from positions 27, 105, 117, 119 and 128, by comparing sequence to Ole1 sequence SEQ ID NO: 1 provided herein (sesame oleosin sequence), and further comprises cysteine amino acid replacements at amino acids selected from positions 3, 12, 23, 112, 123 and 136, by comparing sequence to Ole1 sequence SEQ ID NO: 1 provided herein (sesame oleosin sequence). Notably, in accordance with this aspect, native lysine amino acid 123 is replaced with cysteine. In one aspect, mutant oleosin comprises arginine replacements for lysine at each of amino acid residues 27, 105, 117, 119 and 128, by comparing sequence to Ole1 sequence SEQ ID NO: 1 provided herein (sesame oleosin sequence), and further comprises cysteine amino acid replacements at amino acids 3, 12, 23, 112, 123 and 136, by comparing sequence to Ole1 sequence SEQ ID NO: 1 provided herein (sesame oleosin sequence). In one such aspect, exemplary mutant oleosin designated Cys_OLE1_KR comprises cysteine mutations at each of amino acids 3, 12, 23, 112, 123 and 136 and further comprises arginine at amino acids 27, 105, 117, 119 and 128. Cys_Ole_KR is described herein and in FIG. 3 and in corresponds to SEQ ID NO:4.

The invention contemplates mutant oleosins wherein one or more of oleosin residues 27, 105, 117, 119, 123 and 128 are replaced with arginine and wherein one or more of amino acids residues 3, 12, 23, 112, 123 and 136 are replaced with cysteine, wherein the comparable amino acids in any native oleosin for mutation are determined by comparing or aligning any native sequence with SEQ ID NO:1. One skilled in the art can readily undertake such a comparison, as evidenced including in FIG. 4 hereof.

In an aspect of the invention, mutant oleosin is provided comprising one or more arginine replacements at amino acid residues selected from positions 27, 105, 117, 119, 123 and 128, by comparing sequence to Ole1 sequence SEQ ID NO: 1 provided herein (sesame oleosin sequence), and further comprising one or more cysteine amino acid replacements at amino acids selected from positions 3, 12, 23, 112, 123 and 136, by comparing sequence to Ole1 sequence SEQ ID NO: 1 provided herein (sesame oleosin sequence).

Mutant oleosin is provided having one or more amino acids deleted. Mutant oleosin is provided having one amino acid deleted. Mutant oleosin is provided having two amino acids deleted. Mutant oleosin is provided having three amino acids deleted. Mutant oleosin is provided having four amino acids deleted. Mutant oleosin is provided having five amino acids deleted. Mutant oleosin is provided having up to six amino acids deleted. Mutant oleosin is provided having six amino acids deleted. Mutant oleosin is provided having at least 6 amino acids deleted. Thus, in accordance with the invention, amino acids at one or more of or at all of corresponding positions of amino acids 3, 12, 23, 112, 123 and 136, by comparing sequence to Ole1 sequence SEQ ID NO: 1 provided herein (sesame oleosin sequence) are deleted. In exemplary mutant oleosin designated OLE1_Cys_DEL, a mutant oleosin is provided wherein 6 amino acid residues at positions corresponding to amino acids 3, 13, 23, 112, 123 and 136 are deleted. OLE1_Cys_DEL is provided and described herein and in FIG. 3 and in corresponding SEQ ID NO: 5. In the native oleosin sequence provided herein designated OLE1 (SEQ ID NO:1) each of the amino acids E at 3, R at 12, Q at 23, Q at 112, K at 123 and Q at 136 are removed or deleted.

The invention provides an oleosin mutant comprising both or each of amino acid mutations and amino acid deletions. Thus, a mutant oleosin is provided combining all amino acid replacement and deletion aspects as detailed above. In an exemplary such mutant oleosin having combined replacements and deletions, designated OLE1_Cys_DEL_KR, the native lysine was changed to arginine at five locations namely amino acids 27, 105, 117, 119 and 128 and 6 amino acid residues were deleted at positions corresponding to amino acids 3, 13, 23, 112, 123 and 136 (E at 3, R at 12, Q at 23, K at 27, Q at 112, K at 123 and Q at 136 in SEQ ID NO:1). OLE1_Cys_DEL_KR is provided and described herein and in FIG. 3 and in corresponding SEQ ID NO: 6.

In other aspects, mutant oleosins combining one or more arginine amino acid replacement selected from positions 27, 105, 117, 119, 123 and 128, by comparing sequence to Ole1 sequence SEQ ID NO: 1 provided herein, and one or more amino acid deletions at amino acids selected from positions 3, 12, 23, 112, 123 and 136, by comparing sequence to Ole1 sequence SEQ ID NO: 1 provided herein are provided. In such aspects, mutant oleosins combining up to five arginine amino acid replacements selected from positions 27, 105, 117, 119 and 128 and up to six amino acid deletions at amino acids selected from positions 3, 12, 23, 112, 123 and 136, by comparing sequence to Ole1 sequence SEQ ID NO: 1 provided herein are included in the invention.

Mutant oleosin is provided comprising an arginine replacement at amino acid residues at positions 27, 105 and 117 in SEQ ID NO:1 and further comprising an amino acid deletion at amino acid residue positions 12 and 123 in SEQ ID NO:1. The mutant is designated Ole1_5mod. Ole1_5mod is exemplified in the mutant polypeptide sequence as set out in SEQ ID NO:7.

Mutant oleosin is provided comprising an arginine replacement at amino acid residue 27 SEQ ID NO:1 and further comprising an amino acid deletion at amino acid residue positions 12 and 123 in SEQ ID NO:1. The mutant is designated Ole1_3mod. Ole1_3mod is exemplified in the mutant polypeptide sequence as set out in SEQ ID NO: 8.

Expression of the mutant oleosins allows for the creation of stable oil bodies beyond the reproductive tissue of vascular plants into new cell types and even other species. In an aspect, when combined with a TAG synthesizing enzyme, the invention leads to the accumulation and storage of TAG in cells, or in plants or seeds, as stable oil bodies. Compared with an unmodified cell or plant or even one expressing TAG synthesis enzyme and not expressing mutant oleosin(s) as provided herein, the invention allows for the accumulation of TAG in excess levels when compared to TAG accumulation in native or wild type conditions or genetic backgrounds.

In an additional aspect of the invention, the mutant oleosin(s) can also be fused to a protein of interest, to form a fusion protein. The fusion protein (mutant oleosin plus protein of interest) can be recombinantly expressed in a cell or organism or plant. In this way oil bodies containing the expressed fusion proteins can be used to purify and deliver the protein of interest, for a variety of applications. In a further aspect, the mutant oleosin(s) may be labeled, including by attachment to a detectable or functional label.

Nucleic acids or polynucelotides encoding the mutant or variant oleosin polypeptides are also provided. In an embodiment, nucleic acid is provided encoding one or more mutant oleosin as described herein, including mutant oleosin having one or more arginine replacement and one or more amino acid deletion as provided herein. In an embodiment, nucleic acid is provided encoding one or more mutant oleosin as described herein, including mutant oleosin having one or more arginine replacement and one or more cysteine replacement and/or amino acid deletion as provided herein.

In a further embodiment the polynucleotide encodes a fusion protein including the modified oleosin fused to a protein of interest. Preferably the protein of interest is at the N- or C-terminal end of the fusion protein. Methods for recombinantly expressing fusion proteins are well known to those skilled in the art (Papapostolou and Howorka, 2009). Production of the fusion protein of the invention may typically involve fusing the coding sequence of the protein of interest to the coding sequence of the modified oleosin. Such fusion proteins may be included in, or expressed in, the oil bodies of the invention and used to purify and deliver the protein of interest for a variety of applications, as discussed in Roberts et al, (2008).

In a further aspect the invention provides an expression construct comprising a polynucleotide of the invention. In one embodiment the polynucleotide in the construct is operably linked to a promoter sequence. In one embodiment the promoter sequence is capable of driving expression of the polynucleotide in a vegetative tissue of a plant. In another embodiment the promoter sequence is capable of driving expression of the polynucleotide in a seed of a plant. In a further embodiment the promoter sequence is capable of driving expression of the polynucleotide in the pollen of a plant. In a further embodiment the promoter sequence is capable of driving expression of the polynucleotide in a bacterial cell or yeast cell.

In another aspect, the invention provides a construct containing a polynucleotide that encodes a mutant oleosin as provided herein. In one embodiment, the construct also contains a second polynucleotide that encodes a triacylglycerol (TAG) synthesizing enzyme. In various embodiments, the construct can be linked to a promoter sequence capable of driving its expression in various host cells. As such, the invention also provides use of the constructs to induce a host cell to express a modified oleosin and/or a TAG synthesizing enzyme. In various embodiments, the construct expressing a mutant oleosin and the construct expressing a TAG synthesizing enzyme may be driven by the same or by different promoters. In yet another embodiment the construct is located in an appropriate position and orientation of a suitable functional endogenous promoter such that the expression of the construct occurs. In various embodiments, the construct can be expressed in a bacterial, plant, fungal or algal cell. In one embodiment where the construct is expressed in a plant cell, the cell may be of vegetative, seed, pollen or fruit tissue.

In another embodiment the invention provides a host cell comprising a construct and mutant oleosin of the invention.

In an embodiment the invention provides a host cell genetically modified to comprise a polynucleotide of the invention. In a further embodiment the invention provides a host cell genetically modified to express a polynucleotide of the invention.

In a further embodiment the host cell is also genetically modified to express a triacylglycerol (TAG) synthesizing enzyme. In one such aspect, the host cell is genetically modified to comprise a nucleic acid sequence encoding a triacylglycerol (TAG) synthesizing enzyme. In another aspect the host cell comprises an expression construct including a nucleic acid sequence encoding a triacylglycerol (TAG) synthesizing enzyme.

In a further embodiment the nucleic acid is operably linked to a promoter sequence. The promoter sequence may capable of driving expression of the nucleic acid sequence in a vegetative tissue of a plant. In one aspect the promoter sequence is capable of driving expression of the nucleic acid sequence in a seed of a plant or in the pollen of a plant. The promoter sequence may be capable of driving expression of the polynucleotide in a bacterial cell or in a yeast cell.

The host cell may be any suitable type of cell, including a prokaryotic cell or a eukaryotic cell. In one embodiment the host cell is selected from a bacterial cell, a yeast cell, a fungal cell, an insect cell, algal cell, and a plant cell. In a particular embodiment the host cell is a plant cell.

The invention further provides a plant comprising a plant cell of the invention. In one aspect the invention provides a plant comprising a construct of the invention. In an aspect the invention provides a plant genetically modified to comprise or to express a polynucleotide of the invention. In a further embodiment the plant expresses a mutant oleosin provided herein and encoded by the polynucleotide or nucleic acid of the invention. The plant may overexpress the mutant oleosin. In one such embodiment, the plant expresses mutant oleosin at a greater extent, or at a significantly greater extent, than it expresses any native oleosin polypeptde. Thus, the plant expresses more mutant oleosin polypeptide than it does any native or wild type oleosin or related polypeptide. IN an embodiment, the plant cell is engineered to heterologously express the mutant oleosin. The plant cell ordinarily may not express an oleosin or oleosin-type polypeptide. The plant may ordinarily not express any mutant oleosin polypeptide. In an embodiment, the plant cell is engineered to express a mutant form of oleosin polypeptide which is does not naturally or ordinarily produce or express.

In a further aspect, the plant is also genetically modified to express a triacylglycerol (TAG) synthesizing enzyme. In a further embodiment the triacylglycerol (TAG) synthesizing enzyme is expressed in the same tissue as the modified oleosin. In a further embodiment the plant is genetically modified to comprise a nucleic acid sequence encoding a triacylglycerol (TAG) synthesizing enzyme. In a further embodiment the plant comprises an expression construct including a nucleic acid sequence encoding a triacylglycerol (TAG) synthesizing enzyme. In another aspect the plant may be genetically modified to express or overexpress DGAT2 and/or WRI1.

The nucleic acid or polynucleotide of the invention may be operably linked to a promoter sequence. In an aspect, the promoter is suitable and applicable for expression in plants. In an aspect, the promoter is a constitutive promoter. In an aspect, the promoter is an inducible promoter. In an aspect, the promoter is a plant specific promoter, or a promoter directing expression in leaves, tissues or seeds of a plant. In an aspect, the promoter sequence is capable of driving expression of the nucleic acid sequence in a vegetative tissue of a plant. In one embodiment the promoter sequence is capable of driving expression of the nucleic acid sequence in a seed of a plant. In one embodiment the promoter sequence is capable of driving expression of the nucleic acid sequence in the pollen of a plant. In aspects, the promoter may be the constitutive promoter 35S or may be a seed promoter, particularly a strong seed promoter such as the promoter for the gene phaseolin.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

In a further aspect the invention provides an oil body comprising a mutant oleosin, or one or more mutant oleosin(s) of the invention. In a further aspect the invention provides an oil body comprising at least two mutant oleosins of the invention. In one embodiment at least two of the modified oleosins are cross-linked to each other, such as via disulphide bridges and cysteine residues.

In a further aspect the invention provides a composition comprising a mutant oleosin of the invention. In one embodiment the composition comprises the mutant oleosin and a suitable carrier.

The mutant oleosins may be modified naturally occurring oleosins. The plants from which the un-modified or naturally occurring oleosin sequences are derived may be from any plant species that contains oleosins and polynucleotide sequences encoding oleosins. The plant cells in which the mutant oleosins are expressed may be from any plant species. The plants in which the mutant oleosins are expressed may be from any plant species. In one embodiment the plant cell or plant, is derived from a gymnosperm plant species. In a further embodiment the plant cell or plant, is derived from an angiosperm plant species. In a further embodiment the plant cell or plant, is derived from a from dicotyledonous plant species. In a further embodiment the plant cell or plant, is derived from a monocotyledonous plant species. The plant or plant cell may be sugar cane, sorghum or other bioenergy crop. The plant or plant cell may be a non-bioenergy crop.

Biofuel using fast growing and photosynthetically efficient bioenergy crops is emerging as a reliable alternative to fossil fuels. Bioenergy plants increase soil carbon and fix atmospheric carbon. In addition, bioenergy crops (miscanthus, sorghum and poplar) could also be used for the phytoremediation of heavy metal-contaminated soils. Bioenergy crops include specific plants that are grown and maintained at lower costs for biofuel production and are are classified into five types namely, first-, second- and third-generation bioenergy crops, dedicated energy crops and halophytes. The first-generation bioenergy crops include corn, sorghum, rapeseed and sugarcane, whereas the second-generation bioenergy crops are comprised of switchgrass, miscanthus, alfalfa, reed canary grass, Napier grass and other plants. The third-generation bioenergy crops contain boreal plants, crassulacean acid metabolism (CAM) plants, eucalyptus and microalgae. Bioenergy halophytes are comprised of the genera Acacia, *Eucalyptus, Casuarina, Melaleuca, Prosopis, Rhizophora* and *Tamarix*. The dedicated energy crops include perennial herbaceous and woody plant species as giant miscanthus, switchgrass, jatropha and algae.

The relative terms, such as increased and reduced as used herein with respect to plants, are relative to a control plant. Suitable control plants include non-transformed or wild-type versions of plant of the same variety and/or species as the transformed plant used in the method of the invention. Suitable control plants also include plants of the same variety and/or species as the transformed plant that are transformed with a control construct. Suitable control constructs include emptry vector constructs, known to those skilled in the art. Suitable control plants also include plants that have not been transformed with a polynucleotide encoding a modified oleosin including at least one artificially introduced cysteine. Suitable control plants also include plants that do not express a modified oleosin including at least one artificially introduced cysteine.

The term "total lipid" as used herein includes fats, oils, waxes, sterols, glycerol lipids, monoglycerides, diglycerides, phospholipids, monogalactolipids, digalactolipids, phosphatidylcholines, phosphatidylethanolamine, phosphatidylglycerol, phosphatidylinositol, sulfoguinovosyldiacylglycerol, and triglycerides.

The term "oil" as used herein preferably refers to triacylglycerol (TAG).

The term "biomass" refers to the size and/or mass and/or number of vegetative organs of the plant at a particular age or developmental stage. Thus a plant with increased biomass has increased size and/or mass and/or number of vegetative organs than a suitable control plant of the same age or at an equivalent developmental stage. Increased biomass may also involve an increase in rate of growth and/or rate of formation of vegetative organs during some or all periods of the life cycle of a plant relative to a suitable control. Thus increased biomass may result in an advance in the time taken for such a plant to reach a certain developmental stage.

The terms "seed yield", "fruit yield" and "organ yield" refer to the size and/or mass and/or number of seed, fruit or organs produced by a plant. Thus a plant with increased seed, fruit or organ yield has increased size and/or mass and/or number of seeds, fruit or organs respectively, relative to a control plant at the same age or an equivalent developmental stage.

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes.

The technique of hybridizing labelled polynucleotide probes to polynucleotides immobilized on solid supports such as nitrocellulose filters or nylon membranes, can be used to screen the genomic or cDNA libraries. 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilize a sequence identical (or at least highly similar) to that in the plant, for which reduced expression is desired. For these reasons among others, it is desirable to be able to identify and isolate orthologues of a particular gene in several different plant species.

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

A number of plant transformation strategies are available (e.g. Birch, 1997, Ann Rev Plant Phys Plant Mol Biol, 48, 297, Hellens R P, et al (2000) Plant Mol Biol 42:819-32, Hellens R et al Plant Meth 1:13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species. Transformation strategies may be designed to reduce expression of a polynucleotide/polypeptide in a plant cell, tissue, organ or at a particular developmental stage which/when it is normally expressed. Such strategies are known as gene silencing strategies.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9,: 821); cassaya (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463, 174 and 5,750,871); cereals (U.S. Pat. No. 6,074,877); pear (Matsuda et al., 2005, Plant Cell Rep. 24 (1): 45-51); *Prunus* (Ramesh et al., 2006 Plant Cell Rep. 25 (8): 821-8; Song and Sink 2005 Plant Cell Rep. 2006; 25 (2): 117-23; Gonzalez Padilla et al., 2003 Plant Cell Rep. 22 (1): 38-45); strawberry (Oosumi et al., 2006 Planta. 223 (6): 1219-30; Folta et al., 2006 Planta April 14; PMID: 16614818), rose (Li et al., 2003), *Rubus* (Graham et al., 1995 Methods Mol. Biol. 1995; 44:129-33), tomato (Dan et al., 2006, Plant Cell Reports V25: 432-441), apple (Yao et al., 1995, Plant Cell Rep. 14, 407-412), Canola (*Brassica napus* L.). (Cardoza and Stewart, 2006 Methods Mol. Biol. 343:257-66), safflower (Orlikowska et al, 1995, Plant Cell Tissue and Organ Culture 40:85-91), ryegrass (Altpeter et al, 2004 Developments in Plant Breeding 11 (7): 255-250), rice (Christou et al, 1991 Nature Biotech. 9:957-962), maize (Wang et al 2009 In: Handbook of Maize pp. 609-639) and *Actinidia eriantha* (Wang et al., 2006, Plant Cell Rep. 25, 5:425-31). Transformation of other species is also contemplated by the invention. Suitable methods and protocols are available in the scientific literature.

The term "plant" is intended to include a whole plant, any part of a plant, a seed, a fruit, propagules and progeny of a plant.

The term "propagule" means any part of a plant that may be used in reproduction or propagation, either sexual or asexual, including seeds and cuttings.

The plants of the invention may be grown and either selfed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Triacylglycerols (TAG) are amongst the most reduced form of carbon found in plants and are therefore high in energy content. Upon a single methylation or ethylation step TAG is easily converted to biodiesel which can be used as a transportation fuel or as a feedstock to produce specialty chemicals. To make such processes economically viable, it is critical to optimize yields of TAG in either seeds or vegetative tissues. Oleosin (also known as OLE1) is an amphipathic protein that stabilizes oil droplets by forming a coating on their surface that hinders access of lipases which cleave fatty acids (FA) from TAG, initiating the breakdown process. Various groups have overexpressed OLE1 to increase TAG protection, sometimes with other proteins such as DGAT and WR11.

Based on published reports, OLE1 is thought to be degraded after conjugation with ubiquitin. Ubiquitin ligates to proteins via covalent linkage through its C-terminal carboxylate group to a particular lysine (lys), cysteine (cys), serine (ser), threonine (thr) or N-terminus of the target protein. We tested several methods to stabilize the protein by removing residues we expected to be targeted for ubiquitin ligation. During these experiments we also deleted six amino acids from the OLE1 sequence along with the conversion of the lysine to arginine modifications designed to prevent ubiquitin ligation.

Roberts and coworkers engineered a version of the sesame OLE1 that introduced six cysteine residues to replace six naturally-occurring residues, three in the N-terminus of the OLE1 and 3 in the C-terminus (this construct was designated 03-3 in Robert's paper and is herein referred to as Cys-OLE1) (Winichayakul S et al (2013) Plant Physiol 162:626-639). Roberts showed that this Cys-OLE1 construct was able to protect TAG better than native OLE1.

We chose to replace all six lysine residues of the sesame OLE1 (SEQ ID NO: 1) with either arginine residues, to maintain a positive charge at that location, or by alanine residues, the standard neutral mutation that is commonly used for such experiments. We made additional mutant oleosins in which, in addition to the substitutions of arginine residues for lysines, single amino acid deletions were made at each of the locations that had been converted to cysteines by Roberts, resulting in an OLE1 variant that contained five arginine residues at locations occupied by lysine residues in the native OLE1 (SEQ ID NO:1), and that is six residues shorter than that of native OLE1 or of Roberts' cys modified OLE1 (Cys-OLE1).

There was no scientific rationale to deleting amino acids at the six residues substituted for cysteines by Roberts. The design arose serendipitously by error in our ordering a DNA sequence from a computer file that had undergone an incomplete operation. As far as we know there is no precedent for deleting residues that are not known ubiquitin ligation targets with the intention of stabilizing a protein. Thus, the stabilization of OLE1 we observed in this variant was both unplanned and unanticipated. The experimental data provided herein shows the effects of each of these changes on TAG accumulation in leaves of *Nicotiana benthamiana* transiently expressing the constructs as indicated.

The constructs we generated were as follows (amino acid numbers in native sesame OLE1 and SEQ ID NO: 1 are referenced):

OLE1 KR—is a form of Oleosin where at 6 locations the Lysine was changed to Arginine [27, 105, 117, 119, 123 and 128]. According to the data presented, the disclosed mutated form in a transient expression system shows higher TAG (slightly more than 0.3% DW of TAG) compared to wild type (0.25% DW of TAG) or the Cys-Oleosin (slightly less than 0.25% DW of TAG) that was engineered by Roberts (that showed increased TAG when Cys-Oleosin was co-expressed with acyl-CoA: diacylglycerol acyltransferase (DGAT) in a stable transgenic);

Cys_OLE1_KR—is the Cys-Oleosin (Roberts) plus at 5 amino acid locations the lysine was changed to arginine [27, 105, 117, 119 and 128]. According to the data presented, the disclosed mutated form in a transient expression system shows higher TAG (~ 0.3% DW of TAG) compared to wild type (0.25% DW of TAG) or the Cysteine Oleosin (slightly less than 0.25% DW of TAG) that was engineered by Roberts (that showed increased TAG when Cys-Oleosin was co-expressed with acyl-CoA: diacylglycerol acyltransferase (DGAT) in a stable transgenic);

OLE1_Cys_DEL-6 amino acid residues at positions (E at 3, R at 12, Q at 23, Q at 112, K at 123 and Q at 136) were removed. According to the data presented, the disclosed mutated form in a transient expression system shows higher TAG (~ 0.3% DW of TAG) compared to wild type (0.25% DW of TAG) or the Cys-Oleosin (slightly less than 0.25% DW of TAG) that was engineered by Roberts (that showed increased TAG when Cysteine Oleosin was co-expressed with acyl-CoA: diacylglycerol acyltransferase (DGAT) in a stable transgenic);

OLE1_Cys_DEL_KR—At 5 locations the lysine was changed to arginine [27, 105, 117, 119 and 128] and 6 amino acid residues were deleted at positions (E at 3, R at 12, Q at 23, Q at 112, K at 123 and Q at 136). According to the data presented, the disclosed mutated form in a transient expression system shows higher triacylglycerol (TAG) (~0.5% DW of TAG) compared to wild type (0.25% DW of TAG) or the Cys Oleosin (slightly less than 0.25% DW of TAG) that was engineered by Roberts (that showed increased TAG when Cysteine Oleosin was co-expressed with acyl-CoA: diacylglycerol acyltransferase (DGAT) in a stable transgenic).

Figure 1:
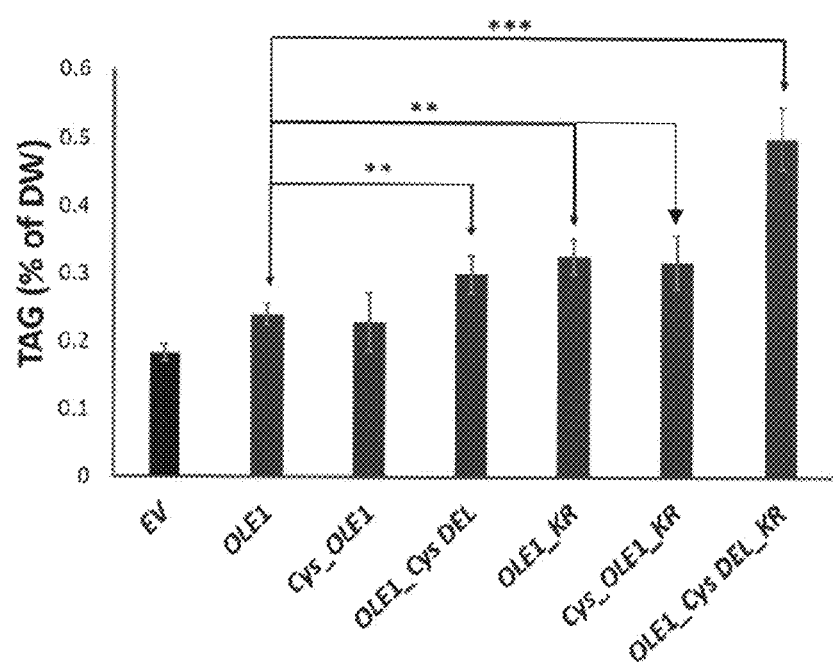
FIG. 1 depicts the evaluation of several oleosin versions in *Nicotiana* bethamiana. Triacyglycerol (TAG) accumulation in the leaves of *N. bethamiana* transiently expressing the following constructs was determined and is provided as a percent of dry weight (% of DW) of the leaves: EV-empty vector; OLE1—refers to native OLE1; Cys_OLE1—refers to mutant OLE1 having 6 Cysteine replacements as previously described (Winichayakul S et al (2013) Plant Physiol 162:626-639); OLE1_CysDel—mutant oleosin having single amino acid deletions at each of the positions corresponding to the Cys mutations in Cys_OLE1; OLE1 KR—oleosin mutated to covert six Lys residues to Arg; Cys_OLE_KR—mutant OLE1 having 6 Cysteine replacements as previously described and also having five Lys residues mutated to Arg; and OLE_CysDEL_KR—mutant oleosin comprising single amino acid deletions at each of the positions corresponding to the Cys mutations in Cys_OLE1 and also having five Lys residues mutated to Arg. Data represents average of at least 4 biological replicates±SD. ** denotes significance at the P<0.01 level and denotes significance at the P<0.001 level.

The results of TAG accumulation in leaves are depicted in FIG. 1. The empty vector (EV), i.e., the mock treatment control showed less than 0.2% TAG. Native OLE1 elevated that slightly to approximately 0.25%, which was not significantly different from the level resulting from the expression of Cys-OLE1 (i.e., Roberts' design). If the amino acids at locations occupied by Cys residues in Roberts Cys_OLE1 were removed to yield an OLE1 variant that is six residues shorter than native OLE1 (designated OLE_Cys_DEL), there is a significant increase in TAG accumulation. Conversion of six lys to arg in the native OLE1 to create OLE1 KR caused a significant increase in TAG accumulation compared to native OLE1. Making the conversion of five lys to arg in the Cys_OLE1 showed an equivalent TAG increase relative to Cys_OLE1 as converting lys to arg in the native OLE1. Combining the two mutant approaches of arginine substitution and amino acid deletions, i.e., deleting the positions of the six Cys and converting all lys to arg in the same construct (named OLE1_CysDel_KR) resulted in a strongly significant increase in TAG accumulation relative to all other constructs. See data in FIG. 1 in which  denotes significance at the $P<0.01$ level and * denotes significance at the $P<0.001$ level.

Thus, we have tested our new variant OLE1 side-by-side with Cys-OLE1 and native OLE1 in the same experiment and shown that our each of our new variants increases TAG accumulation more strongly than Cys-OLE1 and native OLE1. The variant having six amino acid deletions and five arginine replacements showed the most significant increase in TAG accumulation.

Figure 2:
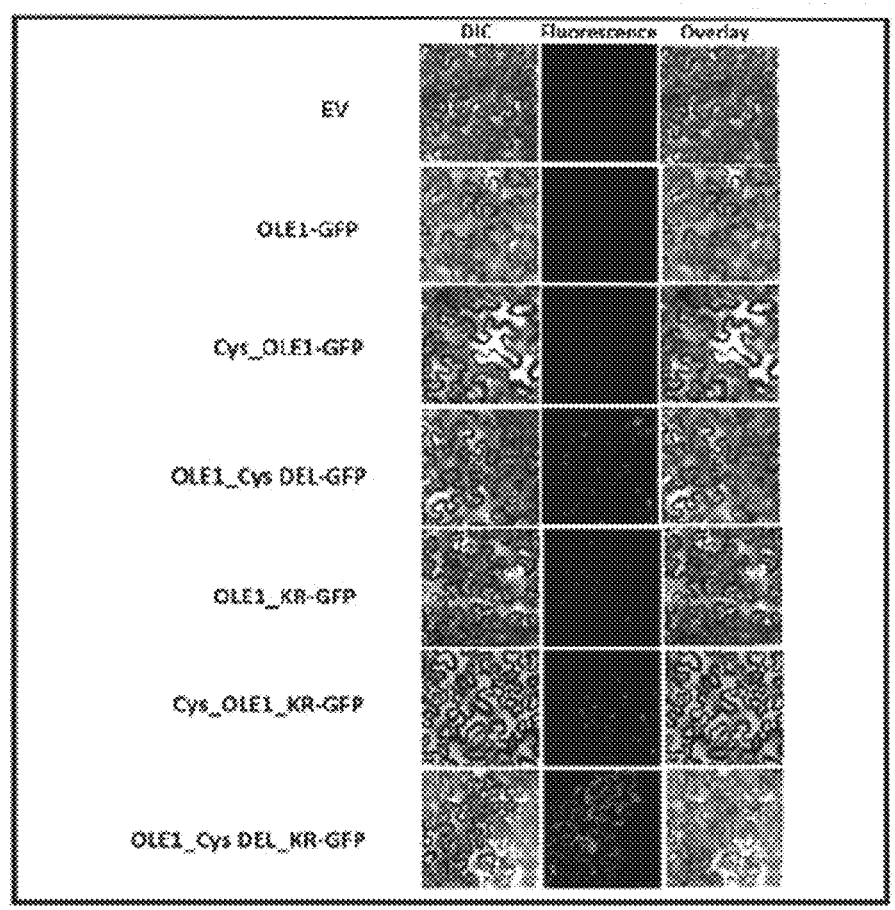
FIG. 2 depicts the effects of OLE1 variants on OLE1 accumulation using GFP-OLE1 fusions. Multiple cysteine deletions (Cys DEL) together with multiple lysine to arginine substitutions (KR) resulted in a cumulative increase in both protein abundance and TAG content. GFP constructs (driven by a 35s promoter) of each of the mutants described in FIG. 1 were generated by C-terminal tagging of the variants with GFP and transiently expressed in *N. bethamiana*. The effects of Cys DEL and KR either singly or in combination were imaged using confocal microscopy in *N. bethamiana*. The extent of fluorescence is indicative of the amount of oleosin accumulating. The results correlate with those observed in FIG. 1.

A further experiment was conducted to show the effect of oleosin variants on protein accumulation in leaves of *Nicotiana benthamiana*. GFP constructs of each of the oleosins were generated and OLE1 accumulation was evaluated as shown in FIG. 2. Cys_OLE I-GFP construct resulted in an increased GFP signal as compared to the Native OLE1-GFP. Upon deletion of each of six amino acid residues occupied by Cysteine in Cys_OLE I resulted in increased GFP signal as compared to both Native OLE1-GFP and Cys_OLE1-GFP. Similar increase of GFP signal was observed upon conversion of lys to arginine OLE1_KR-GFP and Cys_OLE1_KR-GFP as compared to OLE1-GFP and Cys_OLE1-GFP respectively. The best GFP signal was observed in OLE1 C ys DEL_KR-GFP variant containing deletion of six Cys residues and conversion of all lys to arg. The results from these studies correlates with the data that we got for TAG analysis from these OLE1 variants.

The sequence of our OEL1 variants are novel. In particular, each of OLE_CysDEL and OLE_CysDEL_KR represents a truncation of six amino acids at specific sites relative to commonly employed OLE1 constructs such as the native OLE1 and the Cys-OLE1. Despite amino acid deletions, the mutant oleosins result in increased oleosin accumulation and also increased TAG in plant leaves.

A sequence alignment of OLE1 and its variants described herein is provided in FIG. 3. Amino acids shown as black letters on white background represent locations of cysteine residues in Cys-OLE1; amino acids shown in red on white background are the locations of lysine residues in the OLE1 sequence and amino acids shown as white letters on red background are the same in all the sequences: black dots (.) represents an amino acid deletion.

Comparable mutant oleosins can be readily generated based on oleosin sequences from other plants. One can align the alternative native oleosin sequence with our OLE1 (SEQ ID NO:1) and determine the comparable amino acids for mutation or deletion. Numerous oleosin sequences from various plant species are available publicly and in recognized sequence databases such as in Genbank. A comparison and alignment of numerous alternative plant species showing the locations for deletion (4) and/or for K to R replacement (R*) is provided for demonstration in FIG. 4.

We anticipate expressing our variant/mutant oleosin polypeptide(s) in specific tissues such as in seeds with a view to increasing seed oil content and/or expressing it in vegetative tissues to increase TAG accumulation in specific target tissues. We also envisage co-expressing it along with other oleogenic factors such as DGAT1, DGAT2, WRI1, or any other proven oleogenic factor. Evidence from our transient expression in *Nicotiana benthamiana* suggest that expression of the variant OLE1 alone or in combination with other factors leads to increased levels of TAG accumulation compared with the expression of either native OLE1 or Cys-OLE1.

Stable transformation of variant-OLE1 alone and in combination with other oleogenic factors on a variety of promoters, including strong constitutive, vegetative, cell-type specific, or tissue-specific such as seed-specific in a variety of plants including *Arabidopsis*, sugar cane sorghum, and other bioenergy and non-bioenergy crops are envisaged.

REFERENCES

Abell et al., (2004). Plant J., 37:461-70.
Altschul et al., (1997) Nucleic Acids Res. 25:3389-3402.
Andrianov et al., (2010) Plant Biotechnol J. 8 (3): 277-87.
Bairoch and Bucher (1994) Nucleic Acids Res. 22, 3583.
Bao et al, (2000) Plant J. 22 (1): 39-50.
Bari et al., (2009) J. Exp. Bot. 55:623-630.
Birch (1997) Ann Rev Plant Phys Plant Mol Biol, 48, 297.
Bock & Khan (2004) Trends in Biotech. 22:311-318.
Bolton and McCarthy (1962) PNAS 84:1390.
Bowie et al., (1990) Science 247, 1306.
Bouvier-Nave et al., (2000) Eur. J. Biochem. 267, 85-96.
Capuano et al., (2007) Biotechnol Adv. 25:203-206.
Chen et al., (1999) Plant Cell Physiol., 40:1079-1086.
Chiang et al., (2005) J Agric Food Chem 53:4799-804.
Chiang et al., (2007) Protein Expr Purif. 52:14-8.
Chisti (2007) Biotech. Adv. 25:294-306.
Colman et al. (1974) Plant Phys, 53:395-397.
Cookson et al. (2009) Improvements in and relating to oil production.
PCT/NZ2008/000085 WO/2008/130248
Dahlqvist et al (2000) Proc Natl Acad Sci USA. 97, 6487-6492.
Deckers et al (2003) U.S. Pat. No. 6,582,710
Demeyer and Doreau (1999) Proc Nutr Soc. 58 (3): 593-607.
Deutscher (1990) Ed, Methods in Enzymology, Vol. 182, Guide to Protein Purification
Draper et al., 1988, Plant Genetic Transformation and Gene Expression. A Laboratory Manual. Blackwell Sci. Pub. Oxford, p. 365.
Falquet et al., 2002, Nucleic Acids Res. 30, 235.
Feng and Doolittle, 1987, J. Mol. Evol. 25, 351.
Firkins et al., (2006) J Dairy Sci. 89 Suppl 1: E31-51. Review. Greenspan.
Frandsen et al., (2001) Physiologia *Plantarum,* 112:301-307.
Frohman (1993) Methods Enzymol. 218:340-56.
Galun and Breiman (1997) Transgenic Plants. Imperial College Press, London
Gelvin et al., 1993, Plant Molecular Biol. Manual. Kluwer Acad. Pub. Dordrecht
Giesen et al., Nucleic Acids Res. 1998 Nov. 1; 26 (21): 5004-6
Giordano et al., (2005) Ann. Rev. Pl. Biol. 56:99-131.
Halford & Hardie (1998) Plant Mol. Biol. 37:735-48.
Harada et al., (2002) OLEOSIN/PHOSPHOLIPID COMPLEX AND PROCESS FOR
PRODUCING THE SAME. World Patent WO/2002/026788.
Hellens et al., (2000) Plant Mol Biol 42:819-32
Hellens et al., (2005) Plant Meth 1:13.
Herrera-Estrella et al., (1993) Nature 303, 209
Hofmann et al., (1999) Nucleic Acids Res. 27, 215
Hou et al., (2003) J Dairy Sci; 86:424-8.
Huang (1992) Ann. Rev. Plant Physiol. Plant Mol. Biol. 43:177-200.
Huang, X. (1994) Computer Applications in the Biosciences 10, 227-235
Jeanmougin et al., (1998) Trends Biochem. Sci. 23, 403-5.
Jenkins and Bridges (2007) Eur. J. Lipid Sci. Technol. 109:778-789.
Jenkins and McGuire (2006) J Dairy Sci. 89 (4): 1302-10.
Kaup et al., (2002) Plant Physiol. 129 (4): 1616-26.
Kebeish et al., (2007) Nature Biotech, 25:593-599.
Kozaki & Takeba (1996) Nature, 384:557-560.
Kyte and Doolitle (1982) J. Mol. Biol. 157:105-132
Lanfranco L. (2003) Riv Biol. 96 (1): 31-54.
Lardizabal et al., (2001) J. B. C. 276, 38862-38869.
Leprince et al., (1998) Planta 204 109-119.

Lin and Tzen. (2004) Plant Physiology and Biochemistry. 42:601-608.
Lock and Bauman (2004) Lipids. 39 (12): 1197-206.
Loer and Herman (1993) Plant Physiol. 101 (3): 993-998.
Mayer and Fowler (1985) J. Cell Biol. 100 (3): 965-73.
Mekhedov et al., (2000) Plant Physiol. 122 (2): 389-402).
Murphy (1993) Prog. Lipid Res. 32:247-280.
Nakamura et al., (2005) Can. J. Bot. 83:820-833.
Needleman and Wunsch, (1970) J. Mol. Biol. 48, 443-453
Nielsen et al. (1991) Science 254 (5037): 1497-500
Notredame et al., (2000) J. Mol. Biol. 302:205-217
Ohlrogge and Jaworski (1997) Annu Rev Plant Physiol Plant Mol. Biol. 48:109-136.
Papapostolou and Howorka (2009) Mol. Biosyst. 5 (7): 723-32.
Parry et al., (2003) J. Exp. Bot., 54:1321-1333.
Peng et al., (2006) Stability enhancement of native and artificial oil bodies by genipin crosslink. Taiwan patent 1250466.
Peng et al., (2004) J Biotechnol 2004; 111:51-7.
Potrykus and Spangenburg (1995) Gene Transfer to Plants. Springer-Verlag, Berlin
Roberts et al., (2008) The Open Biotechnology Journal 2:13-21.
Roux et al., (2004) J Agric Food Chem. 52 (16): 5245-9.
Scott et al., (2007) Polyoleosins. WO2007045019.
Saha et al., (2006). Plant Physiol. 141 (4): 1533-43.
Sarmiento et al., (1997). Plant J. 11 (4): 783-96.
Schrott (1995) In: Gene Transfer to Plants (Potrykus, T., Spangenberg. Eds) Springer
Verlag. Berline, pp. 325-336
Shimada et al., (2008) Plant J. 55 (5): 798-809.
Shockey et al., (2006) Plant Cell., 18, 2294-2313.
Siloto et al., (2006) Plant Cell. 18 (8): 1961-74.
Slack et al., (1980) Biochem J. 190 (3): 551-561.
Slocombe et al., (2009) Plant Biotechnol J. 7 (7): 694-703.
Stahl et al., (2004) Plant Physiology, 135:1324-1335.
Stewart et al., (1969) In: Solid-Phase Peptide Synthesis, WH Freeman Co, San Francisco Calif.
Thompson et al., (1994) Nucleic Acids Research, 22:4673-4680
Ting et al., (1997). J Biol. Chem., 272:3699-3706.
Tadege et al., (2005). Trends Plant Sci. 10 (5): 229-35.
Triglia et al., 1998, Nucleic Acids Res 16, 8186
Tolbert (1997). Ann. Rev. Pl. Phys. Pl. Molec. Biol. 48:1-25.
Tolbert et al., (1983). Pl. Physiol. 72:1075-1083.
Tzen et al., (1992). J. Biol. Chem. 267:15626-34
Tzen et al., (2003). Adv Plant Physiol., 6:93-104.
Tzen et al., (1997). J. Biochem. 121 (4): 762-8.
Voisey et al., (1994). Plant Cell Reports 13:309 314.
Winichayakul et al., (2008). Proc. NZGA, 70:211-216
Xu et al., (2005). Plant Cell. 17 (11): 3094-110.
Zou et al., (1999). Plant J. 19, 645-653.
Zou et al., (2008). Plant Biotech. J. 6 (8): 799-818.

Example 2

The prior example described various OLE variants/mutants and demonstrated significantly increased TAG accumulation in leaves of *Nicotiana benthamiana* transiently expressing the OLE variants (FIG. 1) and increased protein accumulation in *Nicotiana benthamiana* leaves with transient expression GFP-tagged constructs of the oleosin variants (FIG. 2). OLE variant Ole1_CysDel_KR showed the greatest expression and most significant TAG accumulation of the variants. Ole1_CysDel_KR has a total of eleven (11) amino acid changes compared to native sesame oleosin sequence, particularly an amino acid deletion at each of amino acid residue positions 3, 12, 23, 112, 123 and 136 in native sesame oleosin sequence (SEQ ID NO:1) and additionally has an arginine replacement at each of amino acid residues at positions 27, 105, 117, 119 and 128 in SEQ ID NO:1. To further evaluate the OLE mutants, they were coexpressed with mouse DGAT (mDGAT) to assess TAG accumulation upon co-expression with other oleogenic factors.

Co-expression of OLE1_CysDEL_KR with mDGAT led to more than a 14-fold increase in TAG content upon transient expression in *N. bethamiana* leaves. In order to test the ability of OLE1_CysDEL_KR in protecting TAG in the vegetative tissue, we co-expressed it with a strong mouse DGAT2 (mDGAT). When expressed alone, the OLE1_CysDEL_KR produces a significant increase in TAG content compared to the expression of Cys_OLE1 (FIG. 5). Expression of the mDGAT alone results in 10.6-fold higher TAG content compared to the parental control line (FIG. 5). Upon co-expression of mDGAT with Cys_OLE1, there was no significant increase in TAG content as compared to mDGAT alone. However, co-expression of OLE1_CysDEL_KR with mDGAT resulted in a 14.5-fold increase in TAG content as compared to the control. These results indicate the improved ability of OLE1_CysDEL_KR in protecting TAG as compared to the Cys_OLE1. Further, co-expression with an oleogenic factor such as DGAT leads to an even greater TAG accumulation.

OLE variants/mutants were then evaluated for their effect on lipid (total fatty acid and TAG) accumulation in plant seeds, particularly *Arabidopsis* seeds. *Arabidopsis* overexpression (OE) lines were produced containing oleosin variants under the control of a seed specific promoter—a phaseolin promoter—to assess the effect of CysDel and KR modification either singly or in combination on the storage lipids. The OE lines were generated using a DS red dye screening system. The seeds from the transgenic lines were analyzed for total fatty acid (TFA) and TAG content (FIG. 6). The Ole1_CysDel and CysOle1_KR OE lines resulted in an increase in TFA content when compared to the CysOle1 OE line, but the most significant TFA increase was seen in Ole1_CysDel_KR OE lines. A similar outcome was seen upon analyzing the TAG content, where CysDel and KR modification singly resulted in a significant increase in TAG and combining these modifications together resulted in the highest TAG accumulation as compared to the other tested variants. OLE1_CysDel_KR overexpression resulted in the most significant boost in both total fatty acid and TAG content in *Arabidopsis* seeds.

Example 3

As deletion of cysteine amino acids (CysDel) and substitution of arginine for lysine (KR) modifications were made to all the positions encoding cysteine and lysine residues in the OLE1_CysDel_KR variant, we sought to further evaluate the individual effect (or effects) of these particular deletions or substitutions. It was of interest to assess whether some of these modifications could have a negative effect on oleosin's TAG protection phenotype. In order to gain an insight on the contribution of each of the eleven individual amino acid modifications present in OLE1_CysDEL_KR oleosin, we created a library of OLE1_CysDEL_KR oleosin variants in each of which a single aa modification was substituted back to the aa present in native oleosin.

The following OLE variants/mutants were constructed:

OleNative3 (SEQ ID NO:9) corresponds to OLE1_Cys_DEL_KR with amino acid 3 mutated to the native amino acid glutamic acid (E)

OleNative12 (SEQ ID NO:10) corresponds to OLE1_Cys_DEL_KR with amino acid 12 mutated to the native amino acid arginine (R)

OleNative23 (SEQ ID NO:11) corresponds to OLE1_Cys_DEL_KR with amino acid 23 mutated to the native amino acid glutamine (Q)

OleNative112 (SEQ ID NO:12) corresponds to OLE1_Cys_DEL_KR with amino acid 112 mutated to the native amino acid glutamine (Q)

OleNative123 (SEQ ID NO:13) corresponds to OLE1_Cys_DEL_KR with amino acid 123 mutated to the native amino acid lysine (K)

OleNative136 (SEQ ID NO:14) corresponds to OLE1_Cys_DEL_KR with amino acid 136 mutated to the native amino acid glutamine (Q)

OleK27 (SEQ ID NO: 15) corresponds to OLE1_Cys_DEL_KR with amino acid 27 mutated to the native amino acid lysine (K)

OleK105 (SEQ ID NO:16) corresponds to OLE1_Cys_DEL_KR with amino acid 105 mutated to the native amino acid lysine (K)

OleK117 (SEQ ID NO:17) corresponds to OLE1_Cys_DEL_KR with amino acid 117 mutated to the native amino acid lysine (K)

OleK119 (SEQ ID NO:18) corresponds to OLE1_Cys_DEL_KR with amino acid 119 mutated to the native amino acid lysine (K)

OleK128 (SEQ ID NO:19) corresponds to OLE1_Cys_DEL_KR with amino acid 128 mutated to the native amino acid lysine (K)

These eleven different OLE1_CysDEL_KR variants with only ten amino acid modifications were transiently expressed in *N. benthamiana* leaves and were quantified for TAG accumulation. The results are depicted in FIG. 7. The variants where the cys aa deletion was replaced with an aa substitution at position 12 or at position 123 resulted in a large significant decrease in TAG content as compared to OLE1_CysDEL_KR. This demonstrated that deletion of amino acids 12 and 123 contributed significantly to the TAG accumulation found in the OLE_CysDEL_KR variant construct. Also, variants with R to K substitution at positions 105 and 117 resulted in a significant decrease in TAG content, but to a lesser extent when compared to the variants with substitution at 27. The R to K amino acid substitution at positions 3, 23, 112, 119, 128 and 136 caused no significant change in TAG accumulation compared to OLE1_CysDEL_KR. Based on these studies, amino acid modifications in 5 positions particularly at amino acids 12, 27, 105, 117 and 123 in oleosin sequence SEQ ID NO:1 increased the efficiency compared to OLE1_CysDEL_KR oleosin with respect to TAG accumulation. An OLE variant with these 5 amino acid modifications was designated Ole11_5mod.

Overexpression of Ole1_5Mod and co-expression of Ole1_5Mod with a mouse DGAT2 resulted in a large significant boost in TAG content in *N. bethamiana* leaves: The results described above and depicted in FIG. 7 indicated that CysDel at positions 12 and 123 and KR modification at position 27 are most important modifications contributing to achieve an increased TAG content. In addition, KR modification at positions 105 and 117 were also identified as important and significant with respect to TAG accumulation. Therefore, we engineered two variants of oleosin. First, Ole1_3Mod variant with three modifications that includes two deletions at positions 12 and 123 and KR substitution at position 27. The second variant, Ole1_5Mod with five modifications that includes deletions at positions 12 and 123, and KR substitutions at 27, 105 and 117 positions.

Ole1_5mod has a total of five (5) amino acid changes compared to native sesame oleosin sequence, particularly an amino acid deletion at each of amino acid residue positions 12 and 123 in native sesame oleosin sequence (SEQ ID NO:1) and additionally has an arginine replacement at each of amino acid residues at positions 27, 105 and 117 in SEQ ID NO:1. The sequence of Ole1_5mod is provided in FIG. 3 and in SEQ ID NO:7.

Ole1_3mod has a total of three (3) amino acid changes compared to native sesame oleosin sequence, particularly an amino acid deletion at each of amino acid residue positions 12 and 123 in native sesame oleosin sequence (SEQ ID NO:1) and additionally has an arginine replacement at position 27 in SEQ ID NO: 1. The sequence of Ole1_3mod is provided in FIG. 3 and in SEQ ID NO:8.

These OLE1 variants were transiently expressed in *N. benthamiana* leaves (FIG. 8A) and their TAG accumulation compared to that of Ole1_CysDel_KR. An empty vector control was also evaluated. All the variants in FIG. 8A resulted in a significant increase in TAG content compared to the empty vector control. The Ole1_5 Mod variants was associated with the largest significant increase in TAG content.

In order to further evaluate Ole1_5 Mod and Ole1_3Mod in protecting TAG, we co-expressed these variants with mDGAT2 in *N. benthamiana* leaves (FIG. 8B). mDGAT expression alone resulted in a significant TAG accumulation. mDGAT co-expression with either of the OLE variants Ole1 CysDel_KR, Ole1_5 Mod or Ole1_3Mod increased TAG accumulation above TAG accumulation levels observed with expression of any of the mutants alone or mDGAT alone. The co-expression of Ole1_5 Mod with mDGAT resulted in a 22-fold increase in TAG accumulation as compared to the empty vector control, which was significantly higher than that resulting from the expression of mDGAT2 alone or in combination with either Ole1_CysDel_KR or Ole1_3 Mod.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A mutant sesame oleosin (OLE) polypeptide comprising an arginine replacement at one or more amino acid residues selected from positions 27, 105, 117, 119 and 128 in SEQ ID NO: 1 or in SEQ ID NO:20, and an amino acid deletion at one or more amino acid residues selected from positions 3, 12, 23, 112, 123 and 136 in SEQ ID NO: 1 or in SEQ ID NO:20.

2. The polypeptide of claim 1 wherein the mutant sesame oleosin polypeptide comprises:
   (a) an arginine replacement at one or more lysine residues 27, 105, 117, 119 and 128 in SEQ ID NO:1 or in SEQ ID NO:20 and further comprises an amino acid deletion at one or more of amino acid residue positions 3, 12, 23, 112, 123 and 136 in SEQ ID NO: 1 or in SEQ ID NO:20;
   (b) an arginine replacement at lysine residues at positions 27, 105 and 117 in SEQ ID NO: 1 or in SEQ ID NO:20 and further comprises an amino acid deletion at amino acid residue positions 12 and 123 in SEQ ID NO: 1 or in SEQ ID NO:20; or
   (c) an arginine replacement at lysine residue 27 in SEQ ID NO: 1 or in SEQ ID NO:20 and further comprises an amino acid deletion at amino acid residue positions 12 and 123 in SEQ ID NO: 1 or in SEQ ID NO:20.

3. The polypeptide of claim 1 wherein the mutant sesame oleosin has an amino acid sequence as set out in any one of SEQ ID NOs: 2 or 4-19.

4. The polypeptide of claim 3 wherein the mutant oleosin has an amino acid sequence as set out in SEQ ID NO: 6, 7 or 8.

5. The polypeptide of claim 1 wherein expression of the mutant oleosin in a host cell or host plant results in increased levels or accumulation of oleosin in the cell or plant.

6. The polypeptide of claim 1 wherein expression of the mutant oleosin in a host cell or host plant results in increased levels or accumulation of triacylglycerol (TAG) in the cell or plant.

7. An isolated nucleic acid encoding the polypeptide of claim 1.

8. A recombinant vector comprising the nucleic acid of claim 7.

9. A host cell comprising the vector of claim 8.

10. A host cell recombinantly engineered or genetically modified to produce the mutant oleosin polypeptide of claim 1.

11. A host cell recombinantly engineered to overproduce oleosin and/or TAG by introducing nucleic acid encoding the polypeptide of claim 1, wherein the engineered host cell produces more oleosin and/or TAG than a wild type/native host cell.

12. The host cell of claim 11 which is further engineered to express a triacylglycerol (TAG) synthesizing enzyme.

13. The host cell of claim 11 which is further engineered to express one or more of diacylglycerol acyltransferase (DGAT), wrinkled1 (WRL1) or medium chain thioesterase (MCT or T).

14. The host cell of claim 10 wherein the cell is a plant cell.

15. The host cell of claim 10 that produces triacylglycerol.

16. The host cell of claim 10, wherein the host cell is a yeast cell, fungal cell, an animal cell or a plant cell.

17. A host plant comprising a recombinant vector having a nucleic acid encoding a mutant sesame oleosin (OLE) polypeptide, wherein the mutant oleosin has an arginine replacement at one or more amino acid residues selected from positions 27, 105, 117, 119 and 128 in SEQ ID NO: 1 or in SEQ ID NO:20 and further has an amino acid deletion at one or more amino acid residues selected from positions 3, 12, 23, 112, 123 and 136 in SEQ ID NO: 1 or in SEQ ID NO:20.

18. A host plant recombinantly engineered to produce the polypeptide of claim 17.

19. The host plant of claim 17 wherein the plant is a bioenergy crop that is sesame, sugar cane or sorghum.

20. A method for producing an oil body in a host cell, the method comprising: a) engineering the host cell to produce a mutant oleosin of claim 1; and b) culturing the host cell in order to express the mutant oleosin.

21. The method of claim 20, wherein the host cell is engineered in (a) by introducing into the host cell at least one nucleic acid of claim 7.

22. The method of claim 21, further comprising introducing into the host cell in a) a nucleic acid molecule encoding a TAG synthesizing enzyme; and b) culturing the host cell in order to express the modified oleosin and the TAG synthesizing enzyme.

23. The host cell of claim 10, wherein the mutant oleosin polypeptide has an amino acid sequence as set out in SEQ ID NO: 6, 7 or 8.

24. The host cell of claim 10, recombinantly engineered or genetically modified to produce a combination of mutant oleosin polypeptides, wherein the mutant oleosin polypeptides have the amino acid sequence of SEQ ID NO: 6 and of SEQ ID NO: 7.

25. The host cell of claim 11, wherein the mutant oleosin polypeptide has an amino acid sequence as set out in SEQ ID NO: 6, 7 or 8.

26. The host plant of claim 17, wherein the mutant oleosin has an amino acid sequence as set out in SEQ ID NO: 6, 7 or 8.

27. The host plant of claim 17 comprising a recombinant vector encoding a combination of mutant sesame oleosin (OLE) polypeptides, wherein the mutant oleosin polypeptides have the amino acid sequence of SEQ ID NO: 6 and of SEQ ID NO: 7.

28. The method of claim 20, wherein the mutant oleosin has an amino acid sequence as set out in SEQ ID NO: 6, 7 or 8.

29. The method of claim 20, wherein the host cell is engineered to produce a combination of mutant oleosins of claim 1 and wherein the mutant oleosins have the amino acid sequence of SEQ ID NO: 6 and of SEQ ID NO: 7.

* * * * *

SEQUENCE LISTING

<160> NUMBER OF SEQ ID NOS: 23

<210> SEQ ID NO 1
<211> LENGTH: 145
<212> TYPE: PRT
<213> ORGANISM: Sesamum indicum

<400> SEQUENCE: 1

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
        50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
                100                 105                 110

Leu Glu Ser Ala Lys Thr Lys Leu Ala Ser Lys Ala Arg Glu Met Lys
            115                 120                 125

Asp Arg Ala Glu Gln Phe Ser Gln Gln Pro Val Ala Gly Ser Gln Thr
        130                 135                 140

Ser
145

<210> SEQ ID NO 2
<211> LENGTH: 145
<212> TYPE: PRT
<213> ORGANISM: Artificial Sequence
<220> FEATURE:
<223> OTHER INFORMATION: mutant oleosin Ole1_KR

<400> SEQUENCE: 2

Met Ala Glu His Tyr Gly Gln Gln Gln Thr Arg Ala Pro His Leu
1               5                   10                  15

Gln Leu Gln Pro Arg Ala Gln Arg Val Val Arg Ala Ala Thr Ala Val
            20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
        50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Gln
                100                 105                 110

Leu Glu Ser Ala Arg Thr Arg Leu Ala Ser Arg Ala Arg Glu Met Arg
            115                 120                 125

Asp Arg Ala Glu Gln Phe Ser Gln Gln Pro Val Ala Gly Ser Gln Thr
        130                 135                 140

Ser
145

<210> SEQ ID NO 3
<211> LENGTH: 145
<212> TYPE: PRT
<213> ORGANISM: Artificial sequence
<220> FEATURE:
<223> OTHER INFORMATION: mutant oleosin Cys_Ole1

<400> SEQUENCE: 3

```
Met Ala Cys His Tyr Gly Gln Gln Gln Thr Cys Ala Pro His Leu
1               5                   10                  15

Gln Leu Gln Pro Arg Ala Cys Arg Val Val Lys Ala Ala Thr Ala Val
                20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Cys
                100                 105                 110

Leu Glu Ser Ala Lys Thr Lys Leu Ala Ser Cys Ala Arg Glu Met Lys
            115                 120                 125

Asp Arg Ala Glu Gln Phe Ser Cys Gln Pro Val Ala Gly Ser Gln Thr
            130                 135                 140

Ser
145
```

<210> SEQ ID NO 4
<211> LENGTH: 145
<212> TYPE: PRT
<213> ORGANISM: Artificial sequence
<220> FEATURE:
<223> OTHER INFORMATION: mutant oleosin Cys_Ole1_KR

<400> SEQUENCE: 4

```
Met Ala Cys His Tyr Gly Gln Gln Gln Thr Cys Ala Pro His Leu
1               5                   10                  15

Gln Leu Gln Pro Arg Ala Cys Arg Val Val Arg Ala Ala Thr Ala Val
                20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Cys
                100                 105                 110

Leu Glu Ser Ala Arg Thr Arg Leu Ala Ser Cys Ala Arg Glu Met Arg
            115                 120                 125

Asp Arg Ala Glu Gln Phe Ser Cys Gln Pro Val Ala Gly Ser Gln Thr
            130                 135                 140

Ser
```

```
<210> SEQ ID NO 5
<211> LENGTH: 145
<212> TYPE: PRT
<213> ORGANISM: Artificial Sequence
<220> FEATURE:
<223> OTHER INFORMATION: mutant oleosin Ole1_Cys_Del
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 5

Met Ala Xaa His Tyr Gly Gln Gln Gln Thr Xaa Ala Pro His Leu
1               5                   10                  15

Gln Leu Gln Pro Arg Ala Xaa Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Xaa
            100                 105                 110

Leu Glu Ser Ala Lys Thr Lys Leu Ala Ser Xaa Ala Arg Glu Met Lys
        115                 120                 125

Asp Arg Ala Glu Gln Phe Ser Xaa Gln Pro Val Ala Gly Ser Gln Thr
    130                 135                 140

Ser
145

<210> SEQ ID NO 6
<211> LENGTH: 145
<212> TYPE: PRT
<213> ORGANISM: Artificial Sequence
<220> FEATURE:
<223> OTHER INFORMATION: mutant oleosin Ole1_Cys_Del_KR
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
```

```
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 6

Met Ala Xaa His Tyr Gly Gln Gln Gln Thr Xaa Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
            100                 105                 110

Leu Glu Ser Ala Arg Thr Arg Leu Ala Ser Xaa Ala Arg Glu Met Arg
        115                 120                 125

Asp Arg Ala Glu Gln Phe Ser Xaa Gln Pro Val Ala Gly Ser Gln Thr
    130                 135                 140

Ser
145

<210> SEQ ID NO 7
<211> LENGTH: 145
<212> TYPE: PRT
<213> ORGANISM: Artificial sequence
<220> FEATURE:
<223> OTHER INFORMATION: mutant oleosin Ole1_5mod
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid

<400> SEQUENCE: 7

Met Ala Glu His Tyr Gly Gln Gln Gln Thr Xaa Ala Pro His Leu
1               5                   10                  15

Gln Leu Gln Pro Arg Ala Gln Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
```

```
                50                  55                  60
Pro Val Leu Val Pro Ala Val Ile Thr Ile Phe Leu Leu Gly Ala Gly
 65                  70                  75                  80

Phe Leu Ala Ser Gly Gly Phe Gly Val Ala Ala Leu Ser Val Leu Ser
                 85                  90                  95

Trp Ile Tyr Arg Tyr Leu Thr Gly Arg His Pro Pro Gly Ala Asp Gln
                100                 105                 110

Leu Glu Ser Ala Arg Thr Lys Leu Ala Ser Xaa Ala Arg Glu Met Lys
            115                 120                 125

Asp Arg Ala Glu Gln Phe Ser Gln Gln Pro Val Ala Gly Ser Gln Thr
        130                 135                 140

Ser
145

<210> SEQ ID NO 8
<211> LENGTH: 145
<212> TYPE: PRT
<213> ORGANISM: Artificial sequence
<220> FEATURE:
<223> OTHER INFORMATION: mutant oleosin Ole1_3mod
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid

<400> SEQUENCE: 8

Met Ala Glu His Tyr Gly Gln Gln Gln Thr Xaa Ala Pro His Leu
 1               5                  10                  15

Gln Leu Gln Pro Arg Ala Gln Arg Val Val Arg Ala Ala Thr Ala Val
                 20                  25                  30

Thr Ala Gly Gly Ser Leu Leu Val Leu Ser Gly Leu Thr Leu Ala Gly
             35                  40                  45

Thr Val Ile Ala Leu Thr Ile Ala Thr Pro Leu Leu Val Ile Phe Ser
 50                  55                  60

Pro Val Leu Val Pro Ala Val Ile Thr Ile Phe Leu Leu Gly Ala Gly
 65                  70                  75                  80

Phe Leu Ala Ser Gly Gly Phe Gly Val Ala Ala Leu Ser Val Leu Ser
                 85                  90                  95

Trp Ile Tyr Arg Tyr Leu Thr Gly Lys His Pro Pro Gly Ala Asp Gln
                100                 105                 110

Leu Glu Ser Ala Lys Thr Lys Leu Ala Ser Xaa Ala Arg Glu Met Lys
            115                 120                 125

Asp Arg Ala Glu Gln Phe Ser Gln Gln Pro Val Ala Gly Ser Gln Thr
        130                 135                 140

Ser
145

<210> SEQ ID NO 9
<211> LENGTH: 145
<212> TYPE: PRT
<213> ORGANISM: Artificial sequence
<220> FEATURE:
<223> OTHER INFORMATION: mutant oleosin OleNative3
<220> FEATURE:
<221> NAME/KEY: MISC_FEATURE
<222> LOCATION: (12)..(12)
<223> OTHER INFORMATION: X is a deleted amino acid
```

```
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 9

Met Ala Glu His Tyr Gly Gln Gln Gln Thr Xaa Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
            100                 105                 110

Leu Glu Ser Ala Arg Thr Arg Leu Ala Ser Xaa Ala Arg Glu Met Arg
        115                 120                 125

Asp Arg Ala Glu Gln Phe Ser Xaa Gln Pro Val Ala Gly Ser Gln Thr
    130                 135                 140

Ser
145

<210> SEQ ID NO 10
<211> LENGTH: 145
<212> TYPE: PRT
<213> ORGANISM: Artificial sequence
<220> FEATURE:
<223> OTHER INFORMATION: mutant oleosin Ole_Native12
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 10
```

```
Met Ala Xaa His Tyr Gly Gln Gln Gln Thr Arg Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
            100                 105                 110

Leu Glu Ser Ala Arg Thr Arg Leu Ala Ser Xaa Ala Arg Glu Met Arg
            115                 120                 125

Asp Arg Ala Glu Gln Phe Ser Xaa Gln Pro Val Ala Gly Ser Gln Thr
130                 135                 140

Ser
145

<210> SEQ ID NO 11
<211> LENGTH: 145
<212> TYPE: PRT
<213> ORGANISM: Artificial sequence
<220> FEATURE:
<223> OTHER INFORMATION: mutant oleosin Ole_Native 23
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 11

Met Ala Xaa His Tyr Gly Gln Gln Gln Thr Xaa Ala Pro His Leu
1               5                   10                  15

Gln Leu Gln Pro Arg Ala Gln Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
```

```
                    100                 105                 110
Leu Glu Ser Ala Arg Thr Arg Leu Ala Ser Xaa Ala Arg Glu Met Arg
            115                 120                 125

Asp Arg Ala Glu Gln Phe Ser Xaa Gln Pro Val Ala Gly Ser Gln Thr
        130                 135                 140

Ser
145

<210> SEQ ID NO 12
<211> LENGTH: 145
<212> TYPE: PRT
<213> ORGANISM: Artificial sequence
<220> FEATURE:
<223> OTHER INFORMATION: mutant oleosin Ole_Native 112
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 12

Met Ala Xaa His Tyr Gly Gln Gln Gln Gln Thr Xaa Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Gln
            100                 105                 110

Leu Glu Ser Ala Arg Thr Arg Leu Ala Ser Xaa Ala Arg Glu Met Arg
            115                 120                 125

Asp Arg Ala Glu Gln Phe Ser Xaa Gln Pro Val Ala Gly Ser Gln Thr
        130                 135                 140

Ser
145

<210> SEQ ID NO 13
<211> LENGTH: 145
<212> TYPE: PRT
<213> ORGANISM: Artificial Sequence
<220> FEATURE:
<223> OTHER INFORMATION: mutant oleosin Ole_Native 123
<220> FEATURE:
```

<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 13

Met Ala Xaa His Tyr Gly Gln Gln Gln Thr Xaa Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
            100                 105                 110

Leu Glu Ser Ala Arg Thr Arg Leu Ala Ser Lys Ala Arg Glu Met Arg
        115                 120                 125

Asp Arg Ala Glu Gln Phe Ser Xaa Gln Pro Val Ala Gly Ser Gln Thr
    130                 135                 140

Ser
145

<210> SEQ ID NO 14
<211> LENGTH: 145
<212> TYPE: PRT
<213> ORGANISM: Artificial sequence
<220> FEATURE:
<223> OTHER INFORMATION: mutant oleosin Ole_Native136
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid

<400> SEQUENCE: 14

Met Ala Xaa His Tyr Gly Gln Gln Gln Thr Xaa Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
                100                 105                 110

Leu Glu Ser Ala Arg Thr Arg Leu Ala Ser Xaa Ala Arg Glu Met Arg
            115                 120                 125

Asp Arg Ala Glu Gln Phe Ser Gln Pro Val Ala Gly Ser Gln Thr
        130                 135                 140

Ser
145

<210> SEQ ID NO 15
<211> LENGTH: 145
<212> TYPE: PRT
<213> ORGANISM: Artificial sequence
<220> FEATURE:
<223> OTHER INFORMATION: mutant oleosin OLeK27
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 15

Met Ala Xaa His Tyr Gly Gln Gln Gln Thr Xaa Ala Pro His Leu
1               5                   10                  15

Gln Leu Gln Pro Arg Ala Xaa Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
50                  55                  60

```
Pro Val Leu Val Pro Ala Val Ile Thr Ile Phe Leu Leu Gly Ala Gly
 65                  70                  75                  80

Phe Leu Ala Ser Gly Gly Phe Gly Val Ala Ala Leu Ser Val Leu Ser
                 85                  90                  95

Trp Ile Tyr Arg Tyr Leu Thr Gly Arg His Pro Pro Gly Ala Asp Xaa
             100                 105                 110

Leu Glu Ser Ala Arg Thr Arg Leu Ala Ser Xaa Ala Arg Glu Met Arg
         115                 120                 125

Asp Arg Ala Glu Gln Phe Ser Xaa Gln Pro Val Ala Gly Ser Gln Thr
 130                 135                 140

Ser
145

<210> SEQ ID NO 16
<211> LENGTH: 145
<212> TYPE: PRT
<213> ORGANISM: Artificial sequence
<220> FEATURE:
<223> OTHER INFORMATION: mutant oleosin OleK105
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 16

Met Ala Xaa His Tyr Gly Gln Gln Gln Thr Xaa Ala Pro His Leu
 1               5                  10                  15

Gln Leu Gln Pro Arg Ala Xaa Arg Val Val Arg Ala Ala Thr Ala Val
                 20                  25                  30

Thr Ala Gly Gly Ser Leu Leu Val Leu Ser Gly Leu Thr Leu Ala Gly
             35                  40                  45

Thr Val Ile Ala Leu Thr Ile Ala Thr Pro Leu Leu Val Ile Phe Ser
 50                  55                  60

Pro Val Leu Val Pro Ala Val Ile Thr Ile Phe Leu Leu Gly Ala Gly
 65                  70                  75                  80

Phe Leu Ala Ser Gly Gly Phe Gly Val Ala Ala Leu Ser Val Leu Ser
                 85                  90                  95

Trp Ile Tyr Arg Tyr Leu Thr Gly Lys His Pro Pro Gly Ala Asp Xaa
             100                 105                 110

Leu Glu Ser Ala Arg Thr Arg Leu Ala Ser Xaa Ala Arg Glu Met Arg
         115                 120                 125

Asp Arg Ala Glu Gln Phe Ser Xaa Gln Pro Val Ala Gly Ser Gln Thr
 130                 135                 140
```

Ser
145

<210> SEQ ID NO 17
<211> LENGTH: 145
<212> TYPE: PRT
<213> ORGANISM: Artificial sequence
<220> FEATURE:
<223> OTHER INFORMATION: mutant oleosin OleK117
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 17

Met Ala Xaa His Tyr Gly Gln Gln Gln Thr Xaa Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
            100                 105                 110

Leu Glu Ser Ala Lys Thr Arg Leu Ala Ser Xaa Ala Arg Glu Met Arg
        115                 120                 125

Asp Arg Ala Glu Gln Phe Ser Xaa Gln Pro Val Ala Gly Ser Gln Thr
    130                 135                 140

Ser
145

<210> SEQ ID NO 18
<211> LENGTH: 145
<212> TYPE: PRT
<213> ORGANISM: Artificial sequence
<220> FEATURE:
<223> OTHER INFORMATION: mutant oleosin OleK119
<220> FEATURE:
<221> NAME/KEY: MISC_FEATURE
<222> LOCATION: (3)..(3)
<223> OTHER INFORMATION: X is a deleted amino acid
<220> FEATURE:

<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid
<220> FEATURE:
<221> NAME/KEY: MISC_FEATURE
<222> LOCATION: (136)..(136)
<223> OTHER INFORMATION: X is a deleted amino acid

<400> SEQUENCE: 18

Met Ala Xaa His Tyr Gly Gln Gln Gln Thr Xaa Ala Pro His Leu
1               5                   10                  15

Gln Leu Gln Pro Arg Ala Xaa Arg Val Val Arg Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Arg His Pro Pro Gly Ala Asp Xaa
            100                 105                 110

Leu Glu Ser Ala Arg Thr Lys Leu Ala Ser Xaa Ala Arg Glu Met Arg
        115                 120                 125

Asp Arg Ala Glu Gln Phe Ser Xaa Gln Pro Val Ala Gly Ser Gln Thr
    130                 135                 140

Ser
145

<210> SEQ ID NO 19
<211> LENGTH: 145
<212> TYPE: PRT
<213> ORGANISM: Artificial sequence
<220> FEATURE:
<223> OTHER INFORMATION: mutant oleosin OleK128
<220> FEATURE:
<221> NAME/KEY: MISC_FEATURE
<222> LOCATION: (3)..(3)
<223> OTHER INFORMATION: X is a deleted amino acid
<220> FEATURE:
<221> NAME/KEY: MISC_FEATURE
<222> LOCATION: (12)..(12)
<223> OTHER INFORMATION: X is a deleted amino acid
<220> FEATURE:
<221> NAME/KEY: MISC_FEATURE
<222> LOCATION: (23)..(23)
<223> OTHER INFORMATION: X is a deleted amino acid
<220> FEATURE:
<221> NAME/KEY: MISC_FEATURE
<222> LOCATION: (112)..(112)
<223> OTHER INFORMATION: X is a deleted amino acid
<220> FEATURE:
<221> NAME/KEY: MISC_FEATURE
<222> LOCATION: (123)..(123)
<223> OTHER INFORMATION: X is a deleted amino acid

```
<220> FEATURE:
<221> NAME/KEY: MISC_FEATURE
<222> LOCATION: (136)..(136)
<223> OTHER INFORMATION: X is a deleted amino acid

<400> SEQUENCE: 19
```

| | | | | | | | | | | | | | | |
|---|---|---|---|---|---|---|---|---|---|---|---|---|---|---|
| Met | Ala | Xaa | His | Tyr | Gly | Gln | Gln | Gln | Thr | Xaa | Ala | Pro | His | Leu |
| 1 | | | | 5 | | | | | 10 | | | | | 15 |
| Gln | Leu | Gln | Pro | Arg | Ala | Xaa | Arg | Val | Val | Arg | Ala | Ala | Thr | Ala | Val |
| | | | 20 | | | | | 25 | | | | | 30 | | |
| Thr | Ala | Gly | Gly | Ser | Leu | Leu | Val | Leu | Ser | Gly | Leu | Thr | Leu | Ala | Gly |
| | | | 35 | | | | | 40 | | | | | 45 | | |
| Thr | Val | Ile | Ala | Leu | Thr | Ile | Ala | Thr | Pro | Leu | Leu | Val | Ile | Phe | Ser |
| | 50 | | | | | 55 | | | | | 60 | | | | |
| Pro | Val | Leu | Val | Pro | Ala | Val | Ile | Thr | Ile | Phe | Leu | Leu | Gly | Ala | Gly |
| 65 | | | | | 70 | | | | | 75 | | | | | 80 |
| Phe | Leu | Ala | Ser | Gly | Gly | Phe | Gly | Val | Ala | Ala | Leu | Ser | Val | Leu | Ser |
| | | | | 85 | | | | | 90 | | | | | 95 | |
| Trp | Ile | Tyr | Arg | Tyr | Leu | Thr | Gly | Arg | His | Pro | Pro | Gly | Ala | Asp | Xaa |
| | | | 100 | | | | | 105 | | | | | 110 | | |
| Leu | Glu | Ser | Ala | Arg | Thr | Arg | Leu | Ala | Ser | Xaa | Ala | Arg | Glu | Met | Lys |
| | | | 115 | | | | | 120 | | | | | 125 | | |
| Asp | Arg | Ala | Glu | Gln | Phe | Ser | Xaa | Gln | Pro | Val | Ala | Gly | Ser | Gln | Thr |
| | 130 | | | | | 135 | | | | | 140 | | | | |
| Ser |
| 145 |

```
<210> SEQ ID NO 20
<211> LENGTH: 145
<212> TYPE: PRT
<213> ORGANISM: Sesame indicum

<400> SEQUENCE: 20
```

| | | | | | | | | | | | | | | |
|---|---|---|---|---|---|---|---|---|---|---|---|---|---|---|
| Met | Ala | Glu | His | Tyr | Gly | Gln | Gln | Gln | Thr | Arg | Ala | Pro | His | Pro |
| 1 | | | | 5 | | | | | 10 | | | | | 15 |
| Gln | Leu | Gln | Pro | Arg | Ala | Gln | Arg | Val | Val | Lys | Ala | Ala | Thr | Ala | Val |
| | | | 20 | | | | | 25 | | | | | 30 | | |
| Thr | Ala | Gly | Gly | Ser | Leu | Leu | Val | Leu | Ser | Gly | Leu | Thr | Leu | Ala | Gly |
| | | | 35 | | | | | 40 | | | | | 45 | | |
| Thr | Val | Ile | Ala | Leu | Thr | Ile | Ala | Thr | Pro | Leu | Leu | Val | Ile | Phe | Ser |
| | 50 | | | | | 55 | | | | | 60 | | | | |
| Pro | Val | Leu | Val | Pro | Ala | Val | Ile | Thr | Ile | Phe | Leu | Leu | Gly | Ala | Gly |
| 65 | | | | | 70 | | | | | 75 | | | | | 80 |
| Phe | Leu | Ala | Ser | Gly | Gly | Phe | Gly | Val | Ala | Ala | Leu | Ser | Val | Leu | Ser |
| | | | | 85 | | | | | 90 | | | | | 95 | |
| Trp | Ile | Tyr | Arg | Tyr | Leu | Thr | Gly | Lys | His | Pro | Pro | Gly | Ala | Asp | Gln |
| | | | 100 | | | | | 105 | | | | | 110 | | |
| Leu | Glu | Ser | Ala | Lys | Thr | Lys | Leu | Ala | Ser | Lys | Ala | Arg | Glu | Met | Lys |
| | | | 115 | | | | | 120 | | | | | 125 | | |
| Asp | Arg | Ala | Glu | Gln | Phe | Ser | Gln | Gln | Pro | Val | Ala | Gly | Ser | Gln | Thr |
| | 130 | | | | | 135 | | | | | 140 | | | | |
| Ser |
| 145 |

```
<210> SEQ ID NO 21
<211> LENGTH: 144
<212> TYPE: PRT
```

<213> ORGANISM: Citrus clementina

<400> SEQUENCE: 21

Met Ala Glu His Tyr Gln Pro His Glu Gln Thr Gln Leu Gln Ser Arg
1               5                   10                  15

Gln Pro Arg Ser His Gln Val Val Lys Ala Ala Thr Ala Val Thr Ala
            20                  25                  30

Gly Gly Ser Leu Leu Val Leu Ser Gly Leu Thr Met Ala Gly Thr Val
        35                  40                  45

Ile Ala Leu Thr Ile Ala Thr Pro Leu Leu Val Ile Cys Ser Pro Val
    50                  55                  60

Leu Val Pro Ala Val Ile Thr Val Ser Leu Leu Ile Met Gly Phe Leu
65                  70                  75                  80

Ala Ser Gly Gly Phe Gly Val Ala Ala Ile Ser Val Leu Ser Trp Ile
                85                  90                  95

Tyr Arg Tyr Val Thr Gly Gly His Pro Pro Gly Ala Asp Gln Leu Glu
            100                 105                 110

Gln Ala Arg Met Lys Leu Ala Ser Lys Ala Arg Glu Met Arg Asp Arg
        115                 120                 125

Ala Glu Gln Phe Gly Gln Gln Ser Thr Gly Ser Gln Pro Gly Ser
    130                 135                 140

<210> SEQ ID NO 22
<211> LENGTH: 146
<212> TYPE: PRT
<213> ORGANISM: Nicotiana sylvestris

<400> SEQUENCE: 22

Met Ala Asp Tyr Tyr Gly Gln Gln His Thr Gln His Gln Gln Leu Asn
1               5                   10                  15

Ser Val Gln Gln Pro Arg Ser His Gln Met Val Lys Ala Ala Thr Ala
            20                  25                  30

Val Thr Ala Gly Gly Ser Leu Leu Val Leu Ser Gly Leu Thr Leu Ala
        35                  40                  45

Gly Thr Val Ile Ala Leu Thr Val Ala Thr Pro Leu Leu Val Ile Phe
    50                  55                  60

Ser Pro Val Ile Val Pro Ala Val Ile Thr Ile Phe Met Leu Val Ser
65                  70                  75                  80

Gly Phe Leu Ala Ser Gly Gly Phe Gly Val Ala Ala Ile Ser Val Leu
                85                  90                  95

Ser Trp Ile Tyr Arg Tyr Val Thr Gly Lys Arg Pro Pro Gly Ala Asp
            100                 105                 110

Gln Leu Glu His Ala Arg His Arg Leu Ala Thr Lys Ala Gly Glu Met
        115                 120                 125

Lys Asp Arg Ala Gln Glu Phe Gly Gln Gln His Val Thr Gly Thr Gln
    130                 135                 140

Gln Gly
145

<210> SEQ ID NO 23
<211> LENGTH: 140
<212> TYPE: PRT
<213> ORGANISM: Punica granatum

<400> SEQUENCE: 23

Met Ala Glu His Gln Ala His Gly Gln His Gln Pro Arg Ser His Gln
1               5                   10                  15

```
Val Val Lys Ala Ala Thr Ala Val Thr Ala Gly Gly Ser Leu Leu Val
        20              25              30

Leu Ser Gly Leu Thr Leu Ala Gly Thr Val Ile Ala Leu Thr Ile Ala
        35              40              45

Thr Pro Leu Leu Val Ile Phe Ser Pro Val Leu Val Pro Ala Val Ile
50              55              60

Thr Val Ala Leu Leu Thr Met Gly Phe Leu Ala Ser Gly Gly Phe Gly
65              70              75              80

Val Ala Ala Leu Thr Val Leu Ser Trp Ile Tyr Arg Tyr Val Thr Gly
            85              90              95

Lys His Pro Pro Gly Ala Asp Gln Ile Asp His Ala Arg Met Lys Leu
            100             105             110

Ala Ser Lys Ala Arg Glu Met Lys Asp Arg Ala Glu Gln Phe Gly Gln
        115             120             125

Gln His Leu Thr Thr Gly Gln Gln Gln Gln Thr Ser
        130             135             140
```